(12) United States Patent
Lysgaard et al.

(10) Patent No.: US 10,584,683 B2
(45) Date of Patent: Mar. 10, 2020

(54) METHOD OF CONDITION MONITORING ONE OR MORE WIND TURBINES AND PARTS THEREOF AND PERFORMING INSTANT ALARM WHEN NEEDED

(71) Applicant: Ventus Engineering GmbH, Vienna (AT)

(72) Inventors: Lars Lysgaard, Odder (DK); Poul Anker Skaarup Lübker, Baar (CH)

(73) Assignee: Ventus Engineering GmbH, Vienna (AT)

( * ) Notice: Subject to any disclaimer, the term of this patent is extended or adjusted under 35 U.S.C. 154(b) by 0 days.

(21) Appl. No.: 16/084,206

(22) PCT Filed: Mar. 9, 2017

(86) PCT No.: PCT/IB2017/051387
§ 371 (c)(1),
(2) Date: Sep. 11, 2018

(87) PCT Pub. No.: WO2017/158479
PCT Pub. Date: Sep. 21, 2017

(65) Prior Publication Data
US 2019/0072082 A1   Mar. 7, 2019

(30) Foreign Application Priority Data

Mar. 14, 2016 (DK) ................................ 2016 70147

(51) Int. Cl.
*F03D 17/00* (2016.01)
*F03D 7/02* (2006.01)
(Continued)

(52) U.S. Cl.
CPC .......... *F03D 17/00* (2016.05); *F03D 7/0204* (2013.01); *F03D 7/0224* (2013.01); *F03D 7/042* (2013.01);
(Continued)

(58) Field of Classification Search
None
See application file for complete search history.

(56) References Cited

U.S. PATENT DOCUMENTS

| 5,305,392 A | 4/1994 | Longest, Jr. et al. |
| 8,511,177 B1 | 8/2013 | Makaremi |

(Continued)

FOREIGN PATENT DOCUMENTS

| DE | 102013110898 A1 | 8/2014 |
| EP | 2025929 A2 | 2/2009 |

(Continued)

*Primary Examiner* — Sean Shechtman
(74) *Attorney, Agent, or Firm* — Dykema Gossett PLLC

(57) ABSTRACT

Disclosed is a method of condition monitoring a WTG (Wind Turbine Generator) comprising acts of collecting and storage of at least the following data sets together with their time stamps. Collection of generator power production measurements. Collection of mechanical status measurements. Collection of generator torque measurements. Collection of nacelle direction measurements. Collection of meteorological conditions measurements. The method compromises a further act of synchronizing the data sets. The invention also relates to a system for condition monitoring a WTG. The invention further relates to a system for visually inspecting a WTG.

23 Claims, 23 Drawing Sheets

(51) Int. Cl.
*F03D 7/04* (2006.01)
*G06T 7/00* (2017.01)

(52) U.S. Cl.
CPC .......... *G06T 7/001* (2013.01); *F05B 2220/30* (2013.01); *F05B 2220/706* (2013.01); *F05B 2260/80* (2013.01); *F05B 2270/1033* (2013.01); *G05B 2219/2619* (2013.01)

(56) References Cited

U.S. PATENT DOCUMENTS

| | | |
|---|---|---|
| 2005/0254045 A1 | 11/2005 | Weiss et al. |
| 2009/0047116 A1 | 2/2009 | Barbu et al. |
| 2009/0266160 A1 | 10/2009 | Jeffrey et al. |
| 2011/0125419 A1 | 5/2011 | Bechhoefer et al. |
| 2011/0133458 A1* | 6/2011 | Harrison ................ F03D 7/046 290/44 |
| 2011/0135466 A1 | 6/2011 | Latorre et al. |
| 2013/0317782 A1* | 11/2013 | Knudsen ................ F03D 7/048 702/187 |
| 2014/0168420 A1 | 6/2014 | Naderhirn et al. |
| 2016/0055400 A1 | 2/2016 | Jorquera et al. |

FOREIGN PATENT DOCUMENTS

| | | |
|---|---|---|
| EP | 2481924 A1 | 8/2012 |
| EP | 2484904 A2 | 8/2012 |
| EP | 2767710 A2 | 8/2014 |
| GB | 2466200 A | 12/2008 |
| WO | 2006047266 A1 | 5/2006 |
| WO | 20090143849 A2 | 12/2009 |
| WO | 2012103668 A1 | 9/2012 |
| WO | 2012152561 A1 | 11/2012 |
| WO | 2015001301 A1 | 1/2015 |
| WO | 2015126203 A2 | 8/2015 |
| WO | 2016008500 A1 | 1/2016 |

* cited by examiner

| Condition Monitoring box - algorithms examples: | | | Level of attention needed and alarm trigger is adjusted according to expert advice, know how, experience and to clients wishes. | | | | | |
|---|---|---|---|---|---|---|---|---|
| Monitor, time stamp and synchronize measurements from A, B, C, D and E makes it possible, using proprietary multidimensional algorithms and relevant analysis, subsequent a regulatory output can be provided related to 1-17 below: | | | | | | | | |
| A) Time stamped generator power production measurements () synchronized with B) Time stamped and synchronized input from sensors installed in the hub, on rotor blades, on main shaft and on nacelle providing position-dependent measurements of movements, accelerations, angles of rotation of the rotor, the individual rotor blades and the tower in x, y and z axis synchronized with C) Time stamped nacelle 360° direction measurement synchronized with | 1) Rotor imbalance monitoring | alarm will trigger according to defined criteria's | | | | | | |
| | 2) Individual blade imbalance monitoring | alarm will trigger according to defined criteria's | | | | | | |
| | 3) Icing on blades monitoring | alarm will trigger according to defined criteria's | | | | | | |
| | 4) Comtamination on blades monitoring | alarm will trigger according to defined criteria's | | | | | | |
| | 5) Individual blade damage monitoring (Also damages due to lightning strike etc.) | alarm will trigger according to defined criteria's | | | | | | |
| | 6) Pitch bearing damage monitoring | alarm will trigger according to defined criteria's | | | | | | |
| | 7) Electrical or hydraulic pitch error monitoring | alarm will trigger according to defined criteria's | | | | | | |
| | 8) Unbalanced mass of individual blades monitoring | alarm will trigger according to defined criteria's | | | | | | |
| | 9) Monitor if there is improved generator power production when yawing | could trigger yaw signal to control system | | | | | | |

Fig. 22A

| | | | | | | | | | |
|---|---|---|---|---|---|---|---|---|---|
| D) Time stamped wind measurements from existing measurement instruments and/or from temporarily installed measurement instruments synchronized with<br>E) Time stamped generator torque measurements. | 10) Monitor if there is improved generator power production when pitching | could trigger pitch signal to control system | | | | | | | |
| | 11) Actual yawed wind inflow angle monitoring | could trigger yaw signal to control system | | | | | | | |
| | 12) Actual turbulence monitoring | could trigger Wind Sector Management signal to control system | | | | | | | |
| | 13) Actual sloped wind inflow angle monitoring | could trigger Wind Sector Management signal to control system | | | | | | | |
| | 14) Actual horizontal wind shear monitoring | could trigger Wind Sector Management signal to control system | | | | | | | |
| | 15) Actual vertical wind shear monitoring | could trigger Wind Sector Management signal to control system | | | | | | | |
| | 16) Unexpected movements in tower monitoring | could trigger Wind Sector Management signal to control system | | | | | | | |
| | 17) Generator power production characteristics | alarm will trigger according to defined criteria's | | | | | | | |

Fig. 22B

| | | |
|---|---|---|
| ☐ | Normal operation | operation is normal and as expected |
| ▨ | Something is wrong | inspection of WTG needed at next service and/or further analysis is needed and elimination of root cause if possible |
| ▥ | ALARM STOP WTG IMMEDIATELY! | WTG do not needed inspection before start up again but further analysis is needed and elimination of root cause if possible |
| ▤ | ALARM something is wrong | WTG can continue operation, but inspection of WTG recommended within x days |
| ▦ | ALARM STOP WTG IMMEDIATELY! | WTG need inspection before start up WTG again |

Fig. 22C

METHOD OF CONDITION MONITORING ONE OR MORE WIND TURBINES AND PARTS THEREOF AND PERFORMING INSTANT ALARM WHEN NEEDED

CROSS-REFERENCE TO RELATED APPLICATIONS

This application is a national stage filing based upon International PCT Application No. PCT/IB2017/051387, filed 09 Mar. 2017, which claims the benefit of priority to Denmark application No. PA201670147, filed 14 Mar. 2016.

FIELD OF THE INVENTION

This invention relates to a method of condition monitoring a WTG (Wind Turbine Generator) comprising acts of collecting and storage of at least the following data sets together with their time stamps. Collection of generator power production measurements. Collection of mechanical status measurements. Collection of generator torque measurements. Collection of nacelle direction measurements. Collection of meteorological conditions measurements. The method compromises a further act of synchronizing the data sets. The invention also relates to a system for condition monitoring a WTG. The invention further relates to a system for visually inspecting a WTG.

BACKGROUND OF THE INVENTION

The rotor blade pitch angles during start up and during operation are essential for any wind turbine's generator power production. For stall-regulated wind turbines the stall level (maximum generator power production) is determined by the air density and the rotor blade pitch angle. For pitch-regulated wind turbines from cut-in wind speed to rated maximum wind turbine generator power production, the blades are supposed to be pitched to extract the maximum power possible. At higher wind speeds and until cut-out wind speed then blades are supposed to be pitched to safely deflect the excess wind power.

It is therefore desirable that the individual blade pitch angles under any rotor position and any wind condition is adjusted correctly to obtain the best possible generator power production and/or to control the turbine max generator power production and loads to be within the specifications. In addition, for both stall regulated wind turbines and pitch regulated wind turbines, if the blade pitch angles of the individual rotor blades at a specific 360° rotor position during start up and operation are not identical, the rotor will not be in balance, resulting in excessive loads on the entire wind turbine and foundation and the generator power production will be influenced in a negative way.

Typically over time the blade pitch system and the blades will experience different kinds of wear and tear and damages during operation as for example stall strips and vortex generators falling off, blade surface cracking and falling off, lightening damages etc. which has a negative impact on the generator power production and loads due to imbalance of the rotor system and reduced aerodynamic efficiency of the individual blades and the entire rotor during operation. This kind of damages is typically inspected only during still stand and by service people using expensive lifts, rope climbing systems or drones.

Over time the blade pitch system will experience mechanical wear and tear and different kinds of damages leading to differences in individual blade pitch angles adjustments etc. during start up and during operation which has a negative impact on the aerodynamic efficiency of the individual blades and the entire rotor and in consequence hereof on generator power production and which will also increase loads.

This kind of mechanical wear and tear related to the blade pitch systems is typically inspected only during still stand and by using traditional camera technology and visual inspection.

Due to production tolerances, from the time of installation there can be different kinds of internal structural differences in the blades and over time there can be changes in the individual blade structure leading to relative blade pitch angle misalignment, difference in blade aerodynamic efficiency, dynamics and imbalance in the rotor system which has a negative impact of the generator power production and increase loads.

This kind of structural changes is typically inspected only during still stand and using different methods.

Any imbalance in the rotor system influence in a negative way the loads on different components in wind turbine, reduce lifetime of those components and lead to consequential damages on for example the foundation etc.

Additionally it is desirable to be able to validate how the blade behaves under different load conditions as variations in the production process might influence the blade's geometry as well as the actual aerodynamic and mechanical function, tolerances and adjustment may influence the individual blade pitch during operation.

Another challenge for condition monitoring of blades, the rotor, generator power production and the tower of a wind turbine is detecting different types of blade damage, any unbalance in individual blade and rotor aerodynamic efficiency, unwanted tower movements and unwanted fluctuations in the generator power production from the wind turbine.

Currently, there is no real-time health overview and condition monitoring of blades and rotors on individual wind turbines and on wind turbine fleets.

Damage can occur right after inspections and this kind of manual inspection is also an expensive process due to WTG down-time during manual inspections, and the process can only be performed under certain weather conditions.

These issues are magnified for offshore locations, where wind farms are considerably larger, salt crystals can be a major cause of erosion and cause moisture diffusion within the blade structure and often the turbines are located far from land and workers must be transported to the off shore site by boat or helicopter every day and the use of lifts and platforms is very difficult due to the swell of the sea.

Consequently, wind farm operators and OEMs have been searching for a condition monitoring system for blades and rotors on individual wind turbines and blades and rotors on wind turbine fleets capable of detecting adverse conditions and predicting failures, in order to help minimize risks and prioritize preventive maintenance and repairs, including strain gauges, acoustics, lasers and thermography—but until now with limited success.

Additional to these facts the basic setting of the traditional condition monitoring wind direction measurement equipment and the wind speed measuring equipment is made during the manufacturing process and typically every second year these instruments are exchanged during service using different positioning and alignment methods, well knowing that these methods are not accurate—due to different accepted tolerances during the manufacturing and servicing process.

Another example is the turbulent fluctuations of wind speed and wind inflow angle impacts on the aerodynamic efficiency of the blades and the entire rotor and influence considerably in a negative way the fatigue life of key components of a wind turbine. Furthermore the generator power production will be influenced in a negative way.

The wind inflow angles can change and the level of turbulence hitting the rotor can be increased or changed under certain conditions, i.e. actual pitch adjustment, operation downstream of another operating wind turbine, downstream of a building or another obstacle, downstream of a patch of trees, downstream of upwind terrain effects as slopes and ridgelines etc.

Today the impact of expected turbulence and relative differences in wind inflow angles will normally be mitigated by having a wind sector management plan which is based on wind measurements on the wind farm sites and "imperfect" computer models and assumptions attempting to predict adverse turbulence loads on the individual wind turbines. Based on these models production output is reduced or wind turbines are shut down at certain wind directions/wind sectors, when the computer calculations conclude such expected conditions where the wind turbulence and wind inflow angle may negatively affect the wind turbine lifetime typical for certain pre-specified combinations of wind direction and wind speed. This measure is called "Wind sector management".

Reducing energy output or shutting down wind turbines obviously lead to a decrease in energy produced by the wind turbine, and this is therefore highly desirable and there is a need for better technologies for measuring and monitoring turbulence and/or wind inflow angle conditions hitting the rotor of individual wind turbines in each wind sector for defining criteria's for a more optimal wind sector management plan only limiting generator power production or shutting down wind turbines when turbulence levels and/or wind inflow angle are actually above permissible limits.

Another example is if the wind direction measurement is not correct, obviously the wind turbine will operate with yaw misalignment, resulting in excessive loads on key components and the entire turbine and the generator power production will be influenced in a negative way.

Thus there is a need for better technologies for measuring and condition monitoring yaw misalignment, relative blade pitch misalignment, turbulence, wind inflow angle etc. which this invention suggest can be done by combining rotor behaviour measurements and generator torque and generator power production measurements for defining criteria's for more optimal yaw and blade pitch algorithms and adds totally new dimensions to this kind of monitoring.

It is therefore highly desirable to have a condition monitoring system combined with a reliable communication system providing instant alarm from and communication to the wind turbine for the receiver to receive earliest possible any instant alarm signal from the wind turbine and for the receiver to be able to stop the operation of the wind turbine remotely when needed to prevent the wind turbine to operate with misalignments, failures to develop or even to prevent catastrophic failures. Traditional communication methods can be used.

On other words Wind Resource Inflow Characteristics, is important for the basic design of a turbine and specifically for managing the operation of the rotor.

However, the nature of our energy source is very variable—it will come from any of the 360 degrees, the density during the year varies and the force of the wind over time changes intensely—you can even find different wind speeds and directions at different rotor heights.

Initially the control algorithms for modern wind turbines were relying on "primitive" wind vanes and anemometers located in turbulences behind the rotor measuring a minimal fraction of the rotor swept area to control the orientation of the rotor into the wind. Today we know that what is measured at hub height in turbulence behind the rotor can be radically different from the wind the entire rotor is seeing, and the control algorithms of new wind turbines are therefore relying on smarter wind vanes and more reliable anemometers, but these instruments are still measuring the wind in turbulences behind the rotor at hub height and now, considering the development in rotor size, in a much smaller fraction of the rotor swept area.

WO 2015/001301 A1 discloses a system for mapping a wind field upwind from a wind turbine. The mapping of the wind field is combined with other sensor elements for data collection used to improved wind turbine performance monitoring and adjustment of the wind turbine by parameters such as blade pitch, yaw control, load management amongst others. The purpose of the system is to improve the performance and protection of the wind turbine by optimized mapping of the wind field.

The system uses the Doppler-effect for mapping the wind field with the novel feature of utilizing a plurality of Doppler beam sources for optimized wind field mapping. A correction factor may be applied to the measured Doppler velocity in order to correct for any known statistical relationship indicating a difference in wind velocity with velocity of particles entrained in the fluid Thereby, achieving to correct the measurement toward the true wind velocity despite potentially inaccurate measurements.

WO 2012/103668 A1 discloses a method and a control system for operating a wind turbine generator based on measured wind condition for achieving an optimized operation of the wind turbine. The method measures wind conditions upwind of the wind turbine at two locations at different distances from the wind turbine and measures operation parameters on the wind turbine. Based on the measurements two generator speeds are calculated: the present generator speed based on measurements on operation measurements on the wind turbine, and a forecasted generator speed based on the measured wind conditions. The operation of the wind turbine is optimized by correcting the generator speed from the calculated present generator speed to the forecasted generator speed. Thereby, achieving a method and a control system for operating a wind turbine, which adjusts the operation of the wind turbine, based on the measured wind conditions in two distances prior to the event of these wind conditions actually hitting the wind turbine, or in other words, achieving a feed-back method with sufficient relevant measured wind data, and with sufficient time to adjust the operation of the wind turbine to the measured wind conditions to improve the power output while preventing overspeed of the wind turbine.

This invention suggest that with combining information from new leading-edge technologies we can now sense and monitoring the wind impact, shear and characteristics of the entire rotor swept area, diagnosing for example electric power fluctuation, tower movements, yaw misalignment of the rotor plane, the actual mechanical function, tolerances and adjustment and the behaviour and the aerodynamic efficiency of individual rotor blades at any 360° position and of the entire rotor at any 360° position and measuring and condition monitoring of turbulence and/or wind inflow angle conditions hitting the rotor on the individual wind turbines.

This new information provided by this invention to the wind turbine controller can be used to optimize the aerodynamic efficiency of the individual blades and of the entire rotor and in consequence hereof obtaining the best possible generator power production and lowest loads to be within the specifications and prevent premature wear and tear on turbine components.

DESCRIPTION OF THE INVENTION

An object of the invention achieved by a method of condition monitoring a WTG (Wind Turbine Generator) comprising acts of collecting and storage of at least the following data sets together with their time stamps. Collection of generator power production measurements. Collection of mechanical status measurements. Collection of generator torque measurements. Collection of nacelle direction measurements. Collection of meteorological conditions measurements.

The method compromises a further act of synchronizing the data sets.

The act of synchronizing data allows for unprecedented verification of individual measures of operational data of a WTG since each measure may be derived from other measures or be dependent on each other. Hence synchronisation allows for improvements in the overall conditioning monitoring of a WTG.

In an example the data is collected or sampled synchronized. In an example the data or time series are arranged and synchronized before processing.

I an example a LiDAR measures the wind conditions say 80 meters in front of the WTG. If the wind speed is 10 m/s the wind conditions will arrive at the WTG after 8 seconds assuming a linear dependency.

Similarly, other measures may reflect events or processed data that are shifted in time by say a few seconds, a few milliseconds etc. Importantly the data should be synchronised at relevant time scales. Thus a person skilled in the art will recognize the time scale of 1-10 seconds for LiDAR systems, and recognize the time scale of say milliseconds to seconds in power production output or generator data and synchronize data accordingly.

An object may be achieved by a method of condition monitoring a WTG (Wind Turbine Generator) comprising acts of collecting data sets with time stamps. The data sets may be A) generator power production measurements; B) mechanical status measurements; C) nacelle direction measurements; D) meteorological conditions measurement including at least wind condition measurements; or E) and torque measurement Handling the data sets say A-E) may involve synchronizing the data sets. There may be acts of processing the data sets to provide at least i) Rotor/blade status information; ii) Generator power production information; iii) Tower status information There may be an act of classifying the information i), ii) and iii) in at least the following states of operation; normal state of operation or non-normal state of operation.

In an embodiment synchronised data sets of A) and B) may provide sufficient or minimal information of improved quality.

In an aspect, data sets A), B), C) and D) are collected, time stamped, stored and synchronized according to a single clock representing the WTG time.

In an aspect, the act of synchronizing is performed using at least one synchronization system for synchronizing collected and time stamped data. The act of classifying at least one automatic self-calibrating processing of the parameters for the classification of the state of operation being adjusted to the individual wind turbine.

Application of a synchronisation ensures synchronized data prior to processing and thus advantageously allow for implementation of calibration of parameters or thresholds in the classification. This may be achieved for an individual WTG.

In an aspect, a yaw misalignment is classified as a normal state of operation.

Prior practice would suggest to the operator that the yaw misalignment should be 0° and thus deviations should be classified as non-normal. However, classifying a misalignment as normal state of operation is advantageous.

In an aspect, the act of processing data to provide yaw misalignment and/or tower status information is via acts of processing data to provide i) Rotor/blade status information and ii) generator power production information from A) power production measurements B) mechanical status measurements or load.

In an aspect, the act of processing data to provide yaw misalignment information and/or tower status information and/or information about wind gusts approaching the wind turbine is via acts of collecting C) nacelle direction measurements and/or D) meteorological conditions measurements from a permanently or temporally installed high precision system and a permanently installed lower precision system corrected/calibrated to the high precision system.

Thus enabling high precision calibration of the algorithm and compare results. When calibrated, lower precision systems may detect events such as gusts and effectively warn against non-normal operational status.

In an aspect, the acts of collecting involves acts of collecting A) time stamped generator power production measurements that are synchronized with B) time stamped sensory input including hub sensory input; rotor blade sensory input, main shaft sensory input, nacelle sensory input that are synchronized with time stamped nacelle/drive train direction measurements; and E) that are synchronized with time stamped torque sensory input. The act of processing involves assessing one of, more of or all of:

Rotor imbalance
Individual blade imbalance
Yaw alignment
Icing on blades
Contamination of blade
Individual blade damage
Pitch bearing damage
Electrical or hydraulic Pitch error
Unbalanced mass of individual blades
Improved (increased or reduced) generator power production from yawing
Improved (increased or reduced) generator power production from pitching blades
Actual Yawed wind inflow angle
Actual turbulence
Actual Sloped wind inflow angle
Actual horizontal wind shear
Abnormal movements in tower
Generator power production classification
Wind gust approaching the rotor An objective may be achieved by a WTG (Wind Turbine Generator) condition monitoring system comprising data set collection means for collecting data sets with time stamps. There may be means for collecting data from one or more of A) means for measuring generator power production output; B) means for measuring mechanical status; C) means for measuring nacelle direction; D) means for measuring meteorological conditions; E) means for measuring torque conditions for the generator. There may be at least one processor configured to process the collected data sets and functionally to generate an output of one or more of: i) Rotor/blade status information; ii) Generator power production information; iii) Tower status information; iv) Wind gust approaching the rotor information. The may be means to generate at least one output of classified information normal state of operation or non-normal state of operation.

In an aspect the system may comprise at least one synchronization system for synchronizing collected and time stamped data. The system may comprise one or more of the following. There may be an option provide information for improved (increased or reduced) generator power production from yawing to be used for automatic control of yawing and other purposes. There may be an option to provide information for improved (increased or reduced) generator power production from pitching blades to be used for automatic control of blade pitching and other purposes. There may be an option to provide information for improved load reduction control by pitching blades to avoid loads from high gusts approaching the wind turbine.

In an aspect, at least one synchronization system for synchronizing collected and time stamping data; and at least one automatic self-calibrating processing of the parameters for the classification of the state of operation being adjusted to the individual wind turbine.

Thus WTG that are different and or installed under different conditions may be fined tuned over a period of time.

An objective is achieved by operating a WTG with a WTG controller based on conditioning monitoring as disclosed herein. The method of operation involves acts of controlling the WTG by feeding the processed at least i) Rotor/blade status information, ii) Generator power production information, and iii) Tower status information to the WTG controller conditionally based on at least the classified states of operation normal state of operation or non-normal state of operation.

Thus operation of the WTG is improved and it is enabled that the WTG can produce more energy whilst at the same time reduce loads on the WTG.

In an aspect of operating a WTG, the states of operation of normal state of operation allows operation where no corrective action signals are applied to the WTG controller or where corrective action signals are applied to the WTG controller; or a non-normal state of operation raises a flag/an alarm requiring the act of manual attendance for continued operation of the WTG.

In an aspect of operating the WTG, the state of operation of normal state of operation involves operating the WTG with yaw misalignment.

This will result in the buffer zone in front to the WTG to be symmetrical and thus distribute the loads more optimal than operating the WTG towards no yaw misalignment.

In an aspect of operating the WTG, the state of operation of non-normal state of operation requires the act of automatic stop of continued operation of the WTG and an act of inspecting the WTG before normal state of operation is resumed.

In an aspect of operating the WTG, the state of operation of non-normal state of operation requires visually inspecting the WTG by acts of pointing a visual inspection system with a field of view about a line of sight of a plane where a the rotor blade, the rotor system and the tower during still stand, start up and during operation will be present. There may be an act of capturing multiple images of the field of view with at least multiple images with at least part of the rotor blade, the rotor system and the tower in the image. There may be an act of selecting at least one reference image amongst the captured images. There may be an act of comparing at least one other captured image with the reference image.

In an aspect of operating the WTG acts of controlling the WTG by feeding the processed at least information for improved (increased or reduced) generator power production from yawing to the WTG controller for controlling automatically alignment (yawing) of the WTG nacelle to positioning the rotor in the optimal wind direction based on improvement of generator power production during yawing as disclosed.

The effect is, that the WTG yaw controller in sequence forces yawing in different directions to search for optimum of generator power production and there by optimal yaw alignment.

In an aspect of operating the WTG, there are acts controlling the WTG by feeding the processed information for improved (increased or reduced) generator power production from pitching blades to the wind turbine controller for controlling WTG blade pitch automatically to positioning the blade in an optimal angle based on improvement of generator power production during blade pitching.

The effect is that the WTG pitch controller in sequence forces the blade pitch angle in different directions to search for optimum of generator power production and there by optimal pitch angle—taking into account the shape of the power curve and actual operational point on the power curve.

In an aspect of operating the WTG, there are acts of controlling the WTG by feeding the processed information about gusts approaching the wind turbine by controlling WTG blade to pitch automatically to positioning the blade in an optimal angle based on improved load control reducing loads from peak wind gusts.

The effect is that the WTG pitch controller forces the blade pitch angle in different directions preparing for more optimum load impact on the WTG rotor—taking into account the wind gust approaching the rotor, actual measured wind speed and the actual operational point on the power curve.

Disclosed is a method of visually inspecting a WTG (Wind Turbine Generator) and parts thereof comprising acts of pointing a visual inspection system with a field of view about a line of sight of a plane where a the rotor blade, the rotor system and the tower during still stand, start up and during operation will be present. There may be an act of capturing multiple images of the field of view with at least multiple images with at least part of the rotor blade the rotor system and the tower in the image. There may be an act of selecting at least one reference image amongst the captured image. There may be an act of comparing at least one other captured image with the reference image.

Thereby is provided a method that effectively analyses and verifies faults on a rotor of a WTG.

The method may be applied in itself or as a method used in conditioning monitoring of a WTG.

In an aspect of visually inspecting a WTG (12) and parts thereof, the visual inspection is carried out by means of one or more line scans.

In an aspect of visually inspecting a WTG and parts thereof, the visual inspection is carried out by means of one or more line scan cameras and one or more area scan cameras.

In an aspect of visually inspecting a WTG and parts thereof, one or more line scan camera is used as a trigger unit to activate one or more area scan camera.

In an aspect of visually inspecting a WTG and parts thereof, phase lock loop (PLL) technology is used for triggering and activation of either one or more line scan cameras and/or one or more area scan camera based on software or methods to synchronize the computer to the real rotor.

The method involves processing the data sets to provide at least one of the following information:
  Rotor imbalance
  Individual blade imbalance
  Yaw alignment
  Icing on blades
  Contamination of blade
  Individual blade damage
  Pitch bearing damage
  Electrical or hydraulic Pitch error
  Unbalanced mass of individual blades
  Improved (increased or reduced) generator power production from yawing
  Improved (increased or reduced) generator power production from pitching blades
  Actual Yawed wind inflow angle
  Actual turbulence
  Actual Sloped wind inflow angle
  Actual horizontal wind shear
  Abnormal movements in tower
  Generator power production classification
  Wind gust approaching the rotor The method may involve an automatic self-calibrating processing of the parameters being adjusted and optimised to the individual wind turbine.

The method may include classifying the processed information in or according to at least the following states of operation: normal state of operation or non-normal state of operation.

Thereby it may be achieved that the individual blade pitch angles under any rotor position and any wind condition may be adjusted correctly to obtain the best possible generator power production and/or to control the turbine max generator power production and loads to be within the specifications. In addition, for both stall regulated wind turbines and pitch regulated wind turbines, if the blade pitch angles of the individual rotor blades at a specific 360° rotor position during start up and operation are not identical, the rotor will not be in balance, resulting in excessive loads on the entire wind turbine and foundation and the generator power production will be influenced in a negative way.

Furthermore it is achieved to have the blade pitch angles during start up and during operation adjusted with an accuracy of 0.2 degrees at a specific 360° rotor position.

According to the invention, if individual pitch of blades is possible on a WTG, an advantage may also be to adjust the individual blade pitch on 1 rotor rpm on large WTG's primarily due to wind speed differences in between top and bottom of the rotor.

According to the invention it enabled to be able to verify and potentially adjust the actual individual blade pitch angles during start up and during operation after installation of the blades on the hub.

In an aspect of the invention the best possible generator power production and/or to control the turbine max generator power production and loads to be within the specifications may be achieved by correct adjustment of the individual blade pitch angles under any rotor position and any wind condition.

In an addition, excessive loads on the entire wind turbine and foundation and the generator power production will be reduced for both stall regulated wind turbines and pitch regulated wind turbines. This may be achieved if the blade pitch angles of the individual rotor blades at a specific 360° rotor position during start up and operation are identical due to that the rotor will be in balance.

As an example 1.0 degree relative blade pitch misalignment will have an influence of roughly 10% reduction on the generator power production level. This generator power production loss may be overcome in one aspect of the invention achieved by an adjustment of an accuracy of 0.2 degrees of the individual blade pitch angles during start up and during operation at a specific 360° rotor position.

In the aspect of the invention blades are installed on the hub, thereby it is achieved to verify and potentially adjust the actual individual blade pitch angles during start up and during operation.

The basic setting of the blade pitch angles is made during installation by matching marks on the hub with marks on the blade root. These marks are made during the manufacturing of the blade. It is well-known that these marks are not accurate due to different accepted tolerances during the production process and thus a misalignment of the blade pitch angles may occur.

Typically, damages to the blade pitch system and the blades arise over time because of different kinds of wear and tear. Additionally, damages during operation as for example stall strips and vortex generators falling off, blade surfaces cracking and falling off, lightening damages etc. are typically observed.

In an aspect of the invention it is achieved to detect damages and misalignment visually by using camera technology additional combined with advanced camera trigger mechanism technology.

In another aspect of the invention damages and misalignment may be detected by condition monitoring of the behaviour and the aerodynamic efficiency of individual rotor blades and the entire rotor during start up and during operation of the wind turbines.

The above mentioned visually detection and condition monitoring may be combined to achieve detection of damages and misalignment.

Thus, theses aspects of the invention provides for information of and instant alarm regarding damages and misalignment during operation. This is highly advantageous and adds totally new dimensions to this kind of inspections and condition monitoring of wind turbine fleets and individual wind turbines.

The abovementioned damages have a negative impact on the generator power production and loads due to imbalance of the rotor system and reduced aerodynamic efficiency of the individual blades and the entire rotor during operation. This kind of damages is typically inspected only during still stand and by service people using expensive lifts, rope climbing systems or drones.

At present only the difference in between the relative blade pitch angles in between the blades installed on the rotor of a wind turbine will be measured at still stand. Typically these measurements are performed by use of a common still camera which is placed underneath the wind turbine rotor. The wind turbine rotor must therefore be stopped in exact positions with the individual blades pointing towards the camera.

However, it is difficult to stop the rotors on the exact position with accuracy low enough to judge the individual blade pitch. Furthermore, it is difficult to interpret these photos. Importantly only the individual relative blade pitch angles can be evaluated by using this method and only when the rotor is not in operation.

In an aspect of the invention it is achieved to visually detect tower movements, individual blade pitch angle and the blade's geometry as well as the actual mechanical function, tolerances and adjustment. This may be achieved both during still stand, start up and during operation of the wind turbines.

This is highly advantageous in regard to maintaining and adjusting WTGs and parts hereof by providing information which may lead to imbalance and misalignment. Imbalance and misalignment may reduce the generator power production and increase loads.

One example that may lead to imbalance and misalignment is that the blade pitch system will experience mechanical wear and tear and different kinds of damages leading to differences in individual blade pitch angles adjustments etc. during start up and during operation.

Another example is that production tolerances may result in different kinds of internal structural differences in the blades, and thus over time there may be changes in the individual blade structure leading to relative blade pitch angle misalignment.

Both examples lead to negative impact on the aerodynamic efficiency of the individual blades, on the entire rotor dynamics and on the balance in the rotor system. This may be overcome by the invention.

Any imbalance in the rotor system influence in a negative way the loads on different components in wind turbine, reduce lifetime of those components and lead to consequential damages on for example the foundation etc.

Variations in the production process may influence the blade's geometry and thus, it may be desirable to validate how the blade behaves under different load conditions The actual aerodynamic and mechanical function, tolerances and adjustment may influence the individual blade pitch during operation.

"The main challenge for condition monitoring of blades, the rotor, generator power production and the tower of a wind turbine is detecting different types of blade damage, any imbalance in individual blade and rotor aerodynamic efficiency, unwanted tower movements and unwanted fluctuations in the generator power production from the wind turbine."

Currently, there is no real-time health overview and condition monitoring of blades and rotors on individual wind turbines and on wind turbine fleets.

For operators, manual inspection therefore continues to be the only option to determine the health of a blade and of the rotor. However, for many reasons this is not an effective solution. Manual inspection involves a visual check of the rotor blades that must be conducted by highly qualified technicians hanging from ropes or using special working platforms. In both cases, the methods depend entirely on the ability to spot damage with the naked eye which means that the manual inspection process is limited to the surface of the rotor blade, or tapping the blade to get an idea of its structural integrity, both of which are widely open to human error.

Furthermore, damage can occur right after inspections and this kind of manual inspection is also an expensive process due to WTG down-time during manual inspections, and the process can only be performed under certain weather conditions.

These issues are magnified for offshore locations, where wind farms are considerably larger, salt crystals can be a major cause of erosion and cause moisture diffusion within the blade structure and often the turbines are located far from land and workers must be transported to the off shore site by boat or helicopter every day and the use of lifts and platforms is very difficult due to the swell of the sea.

Consequently, wind farm operators and OEMs have been searching for a condition monitoring system for blades and rotors on individual wind turbines and blades and rotors on wind turbine fleets capable of detecting adverse conditions and predicting failures, in order to help minimize risks and prioritize repairs, including strain gauges, acoustics, lasers and thermography—but until now with limited success.

Considering measuring wind speed and wind direction to-days standard condition monitoring instruments are located on the nacelle behind the rotor and they are effected from different wind flows around the nacelle, turbulences behind the rotor, actual blade pitch adjustment and the actual site condition i.e. operation downstream of another operating wind turbine, downstream of a building or another obstacle, downstream of a patch of trees depending on from which wind sector the wind is coming etc. and they are therefore not able to measure wind direction and wind speed correctly.

Additional to these facts the basic setting of the condition monitoring wind direction measurement equipment and the wind speed measuring equipment is made during the manufacturing process and typically every second year these instruments are exchanged during service using different positioning and alignment methods, well knowing that these methods are not accurate—due to different accepted tolerances during the manufacturing and servicing process.

Turbulent fluctuations of wind speed and wind inflow angle may impact on the aerodynamic efficiency of the blades and the entire rotor and thereby considerably reduce the lifetime of key components of a wind turbine. Furthermore a reduced aerodynamic efficiency of the blades and the entire rotor also reduces the generator power production.

The wind inflow angles can change and the level of turbulence hitting the rotor can be increased or changed under certain conditions, i.e. actual pitch adjustment, operation downstream of another operating wind turbine, downstream of a building or another obstacle, downstream of a patch of trees, downstream of upwind terrain effects as slopes and ridgelines etc.

Today the impact of expected turbulence and relative differences in wind inflow angles will normally be mitigated by having a wind sector management plan which is based on wind measurements on the wind farm sites and "imperfect" computer models and assumptions attempting to predict adverse turbulence loads on the individual wind turbines. Based on these models production output is reduced or wind turbines are shut down at certain wind directions/wind sectors, when the computer calculations conclude such expected conditions where the wind turbulence and wind inflow angle may negatively affect the wind turbine lifetime typical for certain pre-specified combinations of wind direction and wind speed. This measure is called "Wind sector management".

Reducing energy output or shutting down wind turbines obviously lead to a decrease in energy produced by the wind turbine, and this is therefore highly desirable and there is a need for better technologies for measuring and monitoring turbulence and/or wind inflow angle conditions hitting the rotor of individual wind turbines in each wind sector for defining criteria's for a more optimal wind sector management plan only limiting generator power production or shutting down wind turbines when turbulence levels and/or wind inflow angle are actually above permissible limits.

For example if the wind direction measurement is not correct, obviously the wind turbine will operate with yaw misalignment, resulting in excessive loads on key components and the entire turbine and reduced generator power production.

It is therefore highly advantageous with better technologies for measuring and monitoring yaw alignment for defining criteria's for a more optimal yaw algorithm and adds totally new dimensions to this kind of monitoring.

The overall aerodynamic efficiency of the individual blades and the entire rotor may thus be used as a measuring instrument.

The method of condition monitoring of wind turbine parks and individual wind turbines and parts thereof includes condition monitoring of the behaviour and measuring the aerodynamic efficiency of individual rotor blades and the entire rotor, monitoring of movements in the tower, monitoring the characteristics of generator power production and reliably providing instant alarm—when needed.

According to the present invention there is provided a method for visual inspection of a wind turbine fleet and individual wind turbines rotor blades, rotor and tower. There may be acts of pointing a visual inspection system with a field of view about a line of sight towards a plane area where the rotor blade and potentially also the tower during still stand, start up and operation will be present. There may be acts of capturing multiple images of the field of view with at least multiple images with at least part of the rotor blade in the image. There may be acts of selecting at least one reference image of each blade and potentially also the tower amongst the captured mages. Finally there may be acts of comparing at least one other captured image of each blade and potentially also the tower with the reference image.

Such acts may allow for obtaining the following measures. The acts may allow for inspecting and diagnosing the individual incorrect rotor blade pitch angles during still stand, start up and during operation—subsequent adjusting incorrect rotor blade pitch angles to optimize generator power production from the WTG and at the same time reduce loads to the WTG. The acts may allow for inspecting and diagnosing imbalanced rotors due to varying pitch angles or for other reasons within the rotor system during still stand, start up and during operation can be diagnosed and adjusted leading to increased generator power production and prevention potential damage to other vital WTG components and foundation as a result of reduced loads. The acts may allow for inspecting and diagnosing different kinds of visible blade surface damages on the individual rotor blades during still stand,—subsequent having these damages repaired to optimize generator power production from the WTG and at the same time reduce loads to the WTG.

The acts may allow for inspecting and diagnosing different kinds of rotor blade structural damages only becoming visual during start up and during operations of a wind turbine.

The acts may allow for subsequent having these damages repaired or if repair is impossible have blades exchanged to optimize generator power production from the WTG and at the same time reduce loads to the WTG.

The acts may allow for imbalanced rotors due to different shape, bending, twist, structural differences or for other reasons related to the individual blades on the rotor system during still stand, start up and during operation could be diagnosed and claimed to the supplier for them to fix this problem.

The acts may allow for unexpected and load increasing dynamic behaviour of the wind turbine tower during start up and during operation due to imbalanced rotor system or for other reasons could be diagnosed and claimed to the supplier for them to fix this problem.

The acts may allow for seasonal adjustments of rotor blade pitches due varying climatic temperatures could be more easily performed to optimize the generator power production at the various air densities.

Consequently, by this method rotor blade pitch angle errors, different blade shape, blade bending, blade twist, structural blade differences and unexpected tower dynamics become apparent and can be detected and diagnosed even during start up and operation of the WTG.

In order to improve the method of visually inspecting a rotor blade of a WTG, a rotor and potentially also a tower according to the invention it may be advantageously that the method comprising an act of combining the visual inspection system naturally light and/or with the use of floodlight, laser light, infrared light (thermographic measurements) or other types of light of all kinds to visualize possible surface and/or edge damages of the rotor blade.

It may be advantageously to modify the method according to them invention with the further method step of correlate the measurements with the actual wind speed.

Furthermore it may be an advantage to modify the method according to the invention by an act of correlating the measurements with information's about when the blade pitch system actually are turning the blades.

There may be acts of visually inspecting a rotor blade, a rotor system and potentially also a tower of a WTG according to the invention, where the visual inspection system is a line scan camera.

Alternatively, acts of visually inspecting a rotor blade, a rotor system and potentially also a tower of a WTG according to the invention the visual inspection system is an area scan camera.

Alternatively, acts of visually inspecting a rotor blade, a rotor system and potentially also a tower of a WTG according to the invention the visual inspection system is a thermographic camera.

There may be acts of visually inspecting a rotor blade, a rotor system and potentially also a tower of a WTG according to the invention is such amended, where the visual inspection system is made with a line scan camera and an area scan camera and an thermographic camera individually or in combination.

The acts may be amended or altered so that one or more line scan camera is used as a trigger-unit to activate one or more area scan cameras and/or thermographic cameras.

Furthermore it may be advantageously that the method according to the invention may be such modified that phase lock loop (PLL) technology is used for triggering and activation of either one or more line scan cameras and/or one or more area scan cameras and/or one or more thermic cameras in combination or individually based on software or methods to synchronize the computer to the real rotor behaviour.

A possibility, among others, is to establish a virtual synchronized image of the rotor—as the virtual rotor is a mirror of the real rotor, precise triggering is possible.

The use of especially area scan cameras is the need for exact triggering (capture an image with the rotor in a precise 360° position) may involve making use of a line scan camera able to capture an image of a blade when it is passing the camera view area.

The blade position can then be determinate precisely and the area scan camera or the thermographic camera can be triggered precisely too.

The use may also involve making use of said laser light or any other suitable light sources for activation of a trigger unit for activation of either a line scan camera or an area scan camera or a thermographic camera by the passage of a part preferably an edge part of a WTG rotor blade and the tower during inspection.

The use may also involve making use of said computer controlled triggering for activation of either a line scan camera or an area scan camera or a thermographic camera based on software or methods to synchronize the computer to the real rotor.

Actions may be to establish a virtual synchronized image of the rotor by using PLL technology.

Phase Lock Loop (PLL) technology is commonly used in control systems to synchronizing or locking of machine rotation or electrical signals to a virtual reference signal. As the synchronized virtual rotor is a mirror of the real rotor, precise triggering is possible.

According to a further embodiment of visually inspecting a rotor blade, a rotor system and potentially also a tower of a WTG, there may be further acts. One act may be making use of one or more airborne vehicles for carrying and positioning either one or several line scan cameras or one or more area scan cameras or one or more thermographic cameras. One act may be making use of actual wind speed. It could be an advantage to correlate the measurements with the actual wind speed to have an idea of where on the power curve the wind turbine are operating—therefore it is considered to integrate a small mobile met station into the setup. One act may involve blade pitch system are actually turning. It is an advantage to correlate the measurements with information about when the blade pitch system actually are turning the blades to be able to filter away pictures where the wind turbine pitch system actually are in operation and changing the pitch of the blades.

The visually inspecting of a rotor blade, a rotor system and potentially also a tower of a WTG according to the invention may comprise an act of comparing the captured images with the reference image using pattern recognition technology to accurately determine the relative and absolute rotor blade pitch angle or possible other items of the rotor blade and rotor system being inspected.

There may be acts of providing additional tower dynamics by comparing the captured images with the reference image using pattern recognition technology to accurately determine the absolute tower dynamic being inspected.

Alternatively, the method of visually inspecting a rotor blade, a rotor system and potentially also a tower of a WTG may further involve an act of comparing the captured images, automatically or manually, with the previously captured and stored reference image using pattern recognition technology to establish accurate documentation of the condition of the rotor blade being inspected.

There may be an act of comparing tower movements and the individual blade and the entire rotor measurements with reference values (from other WTG's or from expected values according to measurements of actual meteorological conditions in front of the rotor) to accurate documentation of the condition of the rotor blade and rotor being inspected.

According to another alternative the method of visually inspecting a rotor blade, a rotor system and potentially also a tower of a WTG according to the invention may comprise acts of comparing the captured images with existing construction drawings or other previous documentation using pattern recognition technology to establish accurate documentation of the rotor blade, rotor system and tower being inspected.

There may be an act of comparing tower movements and the individual blade and the entire rotor efficiency measurements with reference values in OEM's specification and documentation to establish accurate documentation of the condition of the rotor blade and rotor being inspected.

According to another alternative the method of visually inspecting a rotor blade, a rotor system and potentially also a tower of a WTG according to the invention may comprise a further act of Comparing the results from "method of visually inspecting a rotor blade, a rotor system and potentially also a tower of a WTG" with results from "method of condition monitoring of wind turbine fleets and individual wind turbines and parts thereof and perform instant alarm when needed"—as described later.

Thereby it is possible to determine a wind turbine's individual rotor blade pitch angles during WTG's start up and normal operation. It is possible to determine a wind turbine's individual rotor blade shape, blade bending, blade twist and structural blade differences etc. during WTG's start up and normal operation. It is possible to determine different kinds of visible blade surface damages on the individual blades during still stand, start up and during operation of a wind turbine. It is possible to determine blade structural damages becoming visual during start up and during operations of a wind turbine. It is possible to determine imbalances in a wind turbine's rotor system during WTG's start up and during operation. It is possible to determine unexpected tower dynamics related to a wind turbine's tower during WTG's start up and during operation by means of dedicated camera technique combined with a computer controlled.

It is possible to precisely triggering for activation of one or more line scan cameras and/or one or more area scan camera and/or one or more thermographic cameras based on software and/or methods to synchronize the computer to the real rotor rpm. recording a WTG's individual rotor blade pitch angles, differences in blade shape, differences in blade temperature, blade bending, blade twist and structural blade differences etc. during start up and normal operation.

It is possible to use of digital photos and pattern recognition technique to record and analyze a WTG's individual rotor blade rotor system and tower.

It is possible to use technical methods for triggering/capture pictures of the blades and blade tips rotor system and tower during stand still, start up and during operation (rotation).

It is possible to use technical methods and algorithms for determination of blade-position, pitch, shape, crew, bending etc. It is possible to optimize a WTG's output using the above mentioned techniques. It is possible to reduce loads on WTG using the above mentioned techniques. It is possible to improve planning of preventive and regular maintenance and as result of this reduce maintenance costs using the above mentioned techniques.

According to the invention there is also provided a method of condition monitoring of wind turbine fleets and individual wind turbines and parts thereof and perform instant alarm when needed.

This invention will be monitoring the WTG's rotor blades, rotor, tower, torque on the generator and generator power production during still stand, start up and during operation where the condition monitoring system or box is configured with one or more features.

There may be means to receive time stamped input about generator power production by use of precision measurement equipment.

There may be means to receive input from accelerometers/sensors installed on rotor blades, in the hub, on main shaft and in the nacelle located in the centre of the tower providing position-dependent measurements of movements, accelerations, angles of rotation of the rotor, the individual rotor blades and the tower in x, y and z axes.

There may be means to receive input about actual torque on the generator from torque measurement equipment.

There may be means to receive input about actual meteorological conditions behind the rotor by use of measurements of wind speed and wind direction etc. measurements from existing measurement instruments located behind the rotor.

There may be means to receive input about nacelle 360° direction.

There may be means to receive software upgrades and input from owner and/or operator to stop the WTG immediately etc.

There may be means to device and organize time stamp and store all above sensor input.

There may be means to synchronize all above sensor inputs.

There may be means to implement use technical methods and multi-dimensional algorithms to process and provide information.

There may be means to automatically self-calibrating processing of the parameters being adjusted to the individual wind turbine.

Thereby is obtained the following measures. Diagnosing actual 360° rotor and 360° blade position-dependent aerodynamic efficiency (converted into the measured generator power production output) by correlating the actual rotor- and blade position measurements of movements, accelerations, angles of rotation of the rotor and the individual rotor blades in x, y and z axes with the actual torque and generator power production—which makes it possible, processing collected data using technical methods and multi-dimensional algorithms, to analyze.

Diagnosing actual rotor and blade 360° position-dependent generator power production.

Diagnosing actual rotor and blade 360° position-dependent movements and accelerations etc.

Diagnosing relatively imbalanced individual blade aerodynamic efficiency due to incorrect alignment of the individual wind turbine blades relative to each other (Relative blade pitch alignment) in any 360° rotor position.

Diagnosing improved/worsened rotor aerodynamic efficiency due to WTG actually is pitching the blades individually or synchronously to a better/worse position.

Diagnosing imbalanced individual blade aerodynamic efficiency in the horizontal direction (with respect to rotor plane) measured at hub height position due to nacelle yaw misalignment.

Diagnosing improved/worsened individual blade aerodynamic efficiency in the horizontal direction (with respect to rotor plane) at hub height position due to WTG actually is yawing the rotor to a better/worse position.

Diagnosing improved/worsened rotor aerodynamic efficiency due to icing on blades and other blade determination reducing the aerodynamic balance and efficiency of the rotor.

Diagnosing unexpected and load increasing imbalanced individual blade aerodynamic efficiency in the tangential direction (with respect to rotor plane) at the top of the rotor position and the bottom of the rotor positions due to wind inflow angle.

Diagnosing unexpected and load increasing imbalanced individual blade aerodynamic efficiency due to turbulence.

Diagnosing unexpected and load increasing imbalanced individual blade aerodynamic efficiency and imbalanced rotors for other reasons within the rotor system during operation as for example wear and tear in the pitch bearing mounts, electrical and hydraulic blade pitch errors or individual rotor blade damage.

Diagnosing unexpected and load increasing imbalanced individual blade aerodynamic efficiency due to different kinds of blade surface damages on the individual rotor blades.

Diagnosing unexpected and load increasing imbalanced mass of the individual blades due to different weight of the individual blades.

Diagnosing aerodynamic efficiency and aerodynamic balance in the entire rotor and unexpected and load increasing imbalance in the individual blade aerodynamic efficiency due to different blade shape, bending, twist, structural differences or for other reasons related to the individual blades on the rotor system.

Diagnosing actual wind speed, wind direction, rotor and blade position-related unexpected and load increasing movements in the tower.

Diagnosing unexpected and unwanted fluctuation and distortion in the electricity network due to any imbalance in the aerodynamic efficiency of the individual rotor blades and the entire rotor.

Diagnosing exact calibrated measurements of the actual generator power production output in a quality which can be used for power curve measurements according to the IEC standard subsequent to above diagnosing Above diagnosing may include taking into consideration expert advice, know how, experience and owners or operators wishes about the level of attention needed and the settings for triggering the instant alarm.

The output may be a regulatory output to the WTG controller which is configured to regulate as a function of this regulatory input to adjusting the incorrect settings for optimizing generator power production from the WTG, and prevention of potential damage to other vital WTG components and foundation as a result of reduced loads to the WTG.

The output may be an instant alarm to the WTG controller when deemed needed.

The output may be an instant alarm to the owner/the operator/24/7 surveillance center when deemed needed for them to arrange adjustment or having the WTG inspected, repaired or if repair is impossible have exchanged arranged (if in warranty period claimed to the supplier for them to fix this problem).

The output may be relevant data and statistics to the owner/operator/24/7 surveillance center as requested for further analysis.

Consequently, by this invention the individual blade and the entire rotor behavior, unexpected loads and tower movements, fluctuations in generator power production etc. become apparent and by using these information it is possible to increase generator power production and at the same time lower loads, maintenance and service costs and extend main component lifetime in a wind turbine by better positioning of the rotor of the WTG and of the individual blades in the wind and furthermore to optimizing wind sector management by providing an improved and refined control signal to the WTG controller or by improving and refining signals directly in the wind turbine controller.

An object may be achieved by a system that comprises at least one processor for processing said input, at least one memory unit for storing said input and the processed output, at least one reliable communication and time synchronization system via satellite or other reliable communication system for providing and receiving instant alarm messages and other relevant information, at least one efficient data transfer option to be able to download larger data amounts from the condition monitoring box, at least one on line connection from the said invention to the WTG controller if output from the invention is integrated in the WTG controller, and at least one permanently installed nacelle direction measurement instrument. There may be at least one measurement device for measuring generator power production output. There may be at least one accelerometer and sensor installed in the hub, on each of the rotor blades, on the main shaft and in the nacelle above the centre of the tower. There may be at least receiving input from one existing measurement instruments located behind the rotor providing input about actual meteorological conditions behind the rotor. There may be input from at least one measurement instruments providing input about actual nacelle direction. There may be at least input from one instrument providing input about actual generator torque.

The system may further be correlating automatically the measurements with input about actual meteorological conditions in front of the rotor provided by a permanently or temporary installed nacelle mounted LiDAR, spinner anemometer or other instruments measuring wind speed and turbulence and potentially also wind direction and wind inflow angle etc. in front or on the rotor and takes into account said stored input about atmospheric conditions obtained by these sensing means.

The system may be correlating manually the measurements from the condition monitoring system with the findings from the method of visual inspection of WTG and parts thereof and take into account said findings.

The system may be comparing the actual measurements, automatically or manually with measurements such as the following. Previous measurements stored from the actual WTG. Reference measurements from similar WTG types. Reference values previously measured from other WTG's with similar rotor configuration. Reference values provided in OEM's or other relevant sources specification and documentation.

The system may add-on additional relevant condition monitoring and measurement instruments to extend the invention to support a Critical Component Condition monitoring, Fault Detection and Instant Alarm System for other key components in a WTG and parts thereof.

The system may be monitoring instant alarm from the wind turbine 24 hours a day/7 days a week in a central surveillance center to prevent failures to develop and catastrophic failure to happen to the WTG and its main components.

This method of condition monitoring of wind turbine fleets and individual wind turbines and parts thereof and perform instant alarm when needed.

The system may be used as a permanently installed tool integrated with the wind turbine controller or signals may be directly integrated and processed in the wind turbine controller on existing and future wind turbines with the purpose to optimize the generator power production and minimize loads, service- and maintenance costs, and automatically to stop the operation of the WTG when deemed needed to prevent failures to develop and catastrophic failures.

The system may be used as a permanently installed stand-alone tool (NOT integrated with the wind turbine controller) on existing and future wind turbines still with the purpose to optimize the generator power production and minimize loads, service- and maintenance costs, and manually to stop the operation of the WTG when deemed needed to prevent failures to develop and to prevent catastrophic failures.

The system may be used to add-on additional relevant condition monitoring and measurement instruments to extend the method and the condition monitoring box to support a Critical Component Condition monitoring, Fault Detection and Instant Alarm System for other key components in wind turbine fleets and individual wind turbines and parts thereof.

The system may eliminate the need of permanent use of one or more complex and expensive systems for detection of atmospheric conditions in front of the rotor. LiDAR, spinner anemometer or other expensive instruments measuring wind speed and wind direction in front of the rotor may be eliminated.

According to this invention then the blades and the rotor can be used as a new innovative measurement instrument for the WTG controller.

The system may also eliminate the need of permanent use of one or more complex and expensive systems for detection of atmospheric conditions behind the rotor.

Existing measurement instruments located behind the rotor measuring wind speed and wind direction behind the rotor may partly be eliminated.

According to this invention then the blades and the rotor can be used as a new innovative measurement instrument for the WTG controller.

In other words according to the invention there is established a new innovative combined technology which represents a step change in the method of condition monitoring of generator power production, a tower, rotor blades and a rotor system of a WTG and reliably providing instant alarm when needed.

This new innovative combined technology monitor a WTG and parts hereof include as minimum condition monitoring of the atmospheric conditions behind the rotor, the nacelle direction, the torque and generator power production, monitoring the behavior of the individual rotor blades and the entire rotor system and the tower, By combining measurements from these technologies the invention provides a technical method and algorithms of condition monitoring, analyzing and optimizing the operational condition of a WTG including the actual entire rotor alignment to the actual wind direction (Yaw alignment) and a measurement of the alignment of the individual wind turbine blades relatively to each other (Relative blade pitch alignment) and the aerodynamic efficiency of the individual blades and the entire rotor in any 360° position (turbulences, wind inflow angle, icing and contamination etc.) and the aerodynamic and mass balance in the rotor and for determination of wear and tear in the pitch bearing mounts, electrical and hydraulic blade pitch errors or individual rotor blade damage, for determination of unexpected movements in the tower and unwanted fluctuations in the generator power production.

By using this new information it hereby becomes possible to make use of recorded values directly in the WTG controller or make use of calculated values from the condition monitoring box directly in the WTG controller to provide new information and significantly improve the quality of the existing sensor signal to the WTG controller. These new and improved and refined control signals makes it possible to increase generator power production and at the same time lower loads, maintenance and service costs and extend main component lifetime in a wind turbine by better positioning of the rotor of the WTG and of the individual blades in the wind and furthermore to optimizing wind sector management.

When deemed needed then the invention will also provide instant alarm to the owner/the operator/24/7 surveillance centre when the WTG should be stopped or inspected to prevent failures to develop and catastrophic failures to happen—and provide information early on if some key exposures aren't performing as expected, and then unscheduled maintenance can be converted into preventive and scheduled service and issues can be handled before a problem becomes crucial and causes very costly failures and prolonged down time.

This will therefore reduce unscheduled maintenance, improve availability, reduce repair costs, repair logistics can be planed more efficiently which considerably will add production and value over the long-term to a WTG portfolio.

This concept specification for a camera system intended for use in visual inspection and optimizations of wind turbine generators. The camera system must be able to focus on long distance and be easy to install, use and take down again.

The overall idea is to provide a visually inspecting method by means of a camera system for use in inspection and optimizations of WTG rotor blades, rotor system and tower in still stand, during start up and during operation of the wind turbine.

There will be at least three advantages of the method according to the invention.

A first advantage is that it allows for performing different diagnostics and analyses of the individual rotor blades rotor system and tower during still stand.

A second advantage is that it allows for performing different diagnostics and analyses of the individual rotor blades rotor system and tower during start-up of the wind turbine.

A third advantage is that it allows for performing different diagnostics and analyses of the individual rotor blades rotor system and tower during operation at different wind speeds.

Diagnostics and analyzes may be focusing on major issues as for example: individual rotor blades pitch angles. Diagnostics may reveal individual rotor blade shape, rotor blade bending, rotor blade twist and structural rotor blade differences etc. Diagnostics may reveal different kinds of visible blade surface damages on the individual rotor blades. Diagnostics may reveal different kinds of rotor blade structural damages only becoming visual during start up and during operations of a wind turbine.

Diagnostics may reveal different kinds of imbalances in rotor system or if different kinds of unexpected tower dynamics related to a wind turbine's tower.

By the means the purpose is to capture high quality pictures of the blades, rotor system and tower during very slow rotation/start up and in full operation at different wind speeds. Related to the blades the task is to measure pitch angle, tip position, rood angle, shape of the blades, bending, twist etc. for the individual blades on a wind turbine so their relative parameters can be compared.

Comparisons to other wind turbines in the same wind farm using the same blades or to wind turbines using the same blades on other locations could also be relevant.

Typically WTG's are located on very windy locations and equipment has to be designed in a way making it easy to install and at the same time stable and usable in all kind of weather conditions.

There are three different camera types or principals for image capturing—line scan camera and area scan camera and thermographic camera.

Pictures of all blades and the rotor system are captured in such a way, that the object appears in the same position ready for comparison.

Pictures of the rotor system and tower are captured in such a way, that the object appears in different positions ready for comparison.

The way to capture pictures is different depending of which camera type is used.

The light is essential for a good camera result. It must be floodlight where the light source can be colored light, white light, UV light, laser light, IR light etc.

Triggering of a line scan camera is not complicated. The camera is free running and record in the timeframe of a rotor round (exc. 5 sec.). Thereby a long picture including all blades is captured.

Area scan camera and thermographic camera has to be triggered exactly when the rotor blade, rotor system and/or tower is in a specific position. High speed cameras are used.

The trigger signal is generated by a computer using PLL technology. Phase lock loop (PLL) is a control system normally used for synchronizing or locking machine rotation or electrical signals to a virtual reference signal.

To create the PLL control loop, it is necessary that the computer can generates triggering pulses to the camera. A PLL solution may be implemented as follows:

1. A virtual movie of a rotor system is created in the computer. The rotor system is rotating randomly.
2. The camera is set in free run and capturing live pictures.
3. By the software: By comparison of the virtual and real movie, the virtual rotor speed and position is tuned in, in such a way, that the virtual rotor reaches the same speed and position as the real rotor. When the virtual rotor covers the real rotor, they are considered to be synchronised.
4. The camera mode setting is changed to triggering mode and the computer is set up to generate triggering signals every time the virtual rotor is in position (same position as in 3).
5. The virtual rotor position, and thereby the triggering position, is slowly turned until the camera capture a image with the blade tip in down position.
6. If the real rotor speed change, the virtual rotor consequently will displace and force a speed change until the displacement is zero and synchronism is reached again.

The object (blade tip picture) is moved or aligned by software so the final result is three pictures with the blade tip in equal positions ready for preceding analysis.

Speed/acceleration alignment: If the rotor change speed during the imaging, the distances on the captured image will change. If the rotor increase speed during imaging, the distance between the blade tip will reduce. (See line scan image in FIG. 5). This contraction will be compensated by "software stretch" so the picture will appear as a constant speed image.

The system will analyze and diagnostic the condition of the individual rotor blade, the rotor system and the tower to emphasize performance improvements and load reductions. Of interest is blade pitch angles, imbalanced rotor and unexpected tower movements. The system creates images clearly exposing these parameters.

DESCRIPTION OF THE DRAWING

The invention is described in more detail in the following reference being made to the accompanying drawing, in which.

The tilt angle of mounting of the rotor (horizontally) with respect to the tower ∈ of the normal 7° between the horizontal plane and the rotor tilted direction to lean the rotor away from the tower to avoid strikes between the blades and the tower.

Figure 17A:
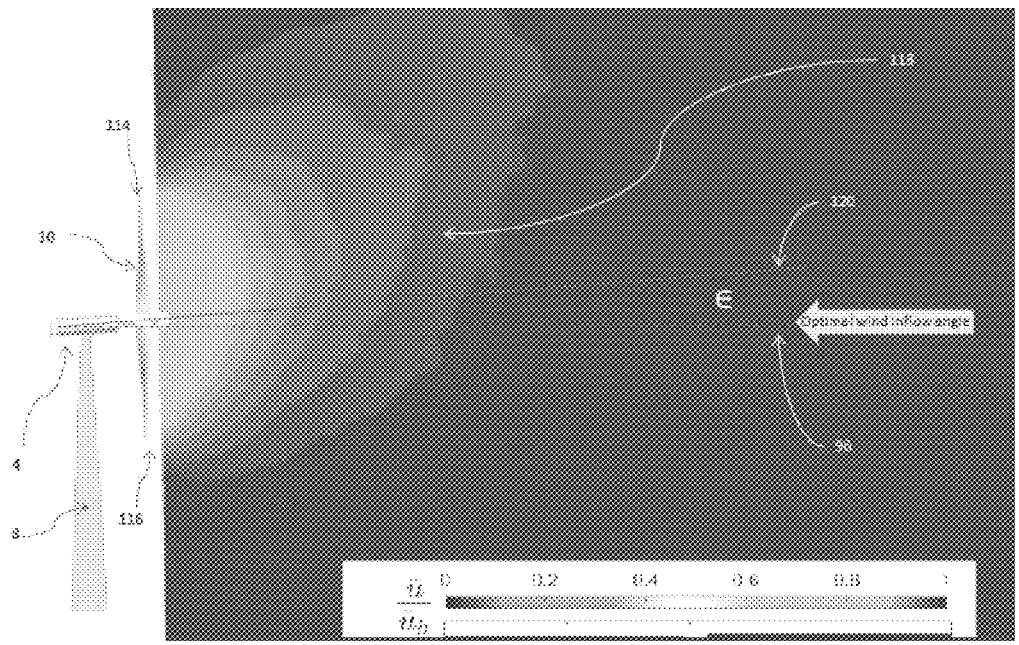
FIG. 17A shows in an image how this invention expect the the contours of the normalized mean stream wise velocity ($u/u_h$) in the tangential directions (with respect to rotor plane) in front of the rotor in the vicinity of the turbine operating with 0° yaw misalignment angle and relatively with the same individual blade pitch angle. The expected contours of the buffer zone can be seen to the right in front of the rotor.
Figure 17B:
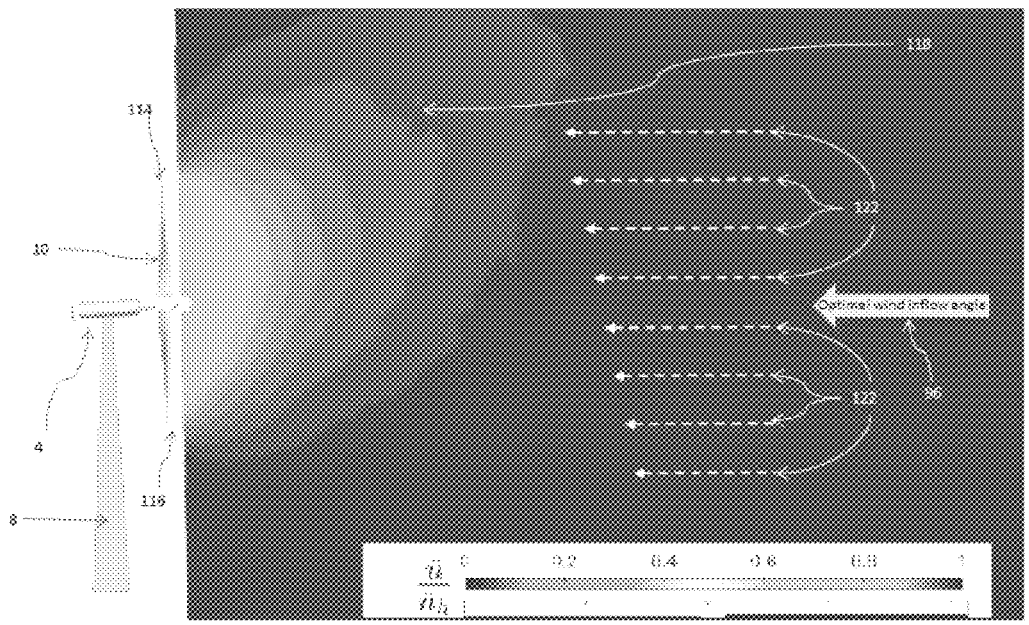

FIG. 17B shows in an image additional to FIG. 17A the wind speed in the tangential direction (with respect to rotor plane) to the right in front of the rotor illustrated by the length of the dotted arrows.

Figure 18:
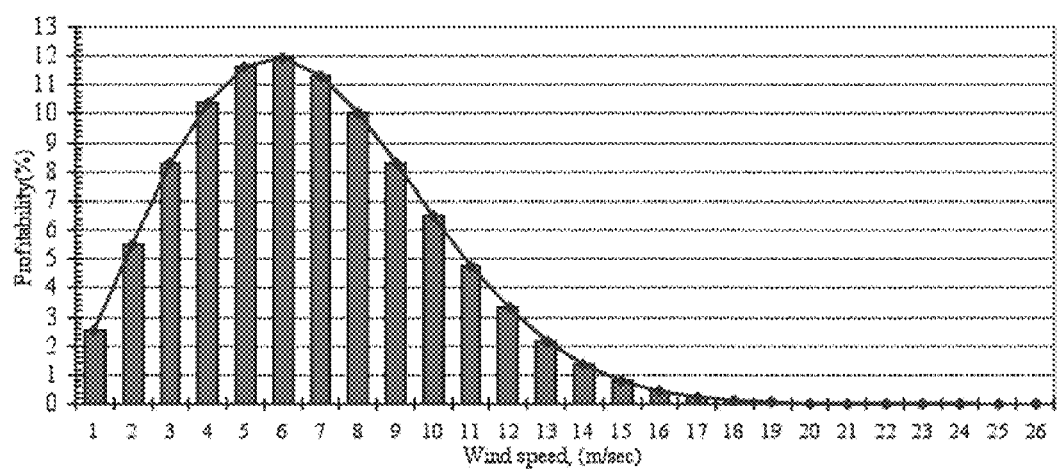
Figure 19A:
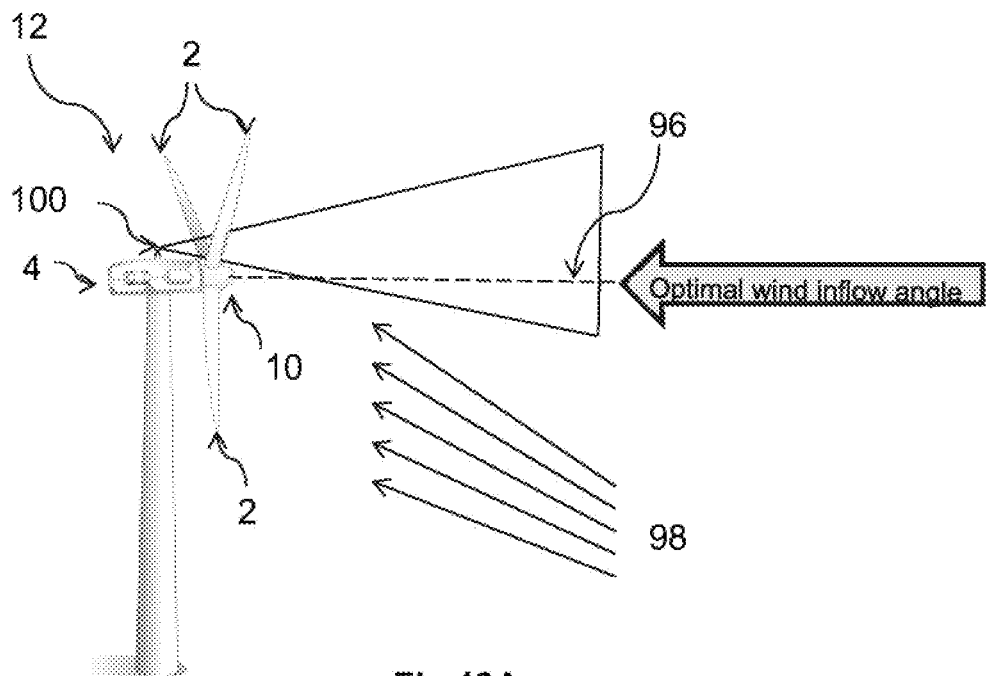
Figure 19B:
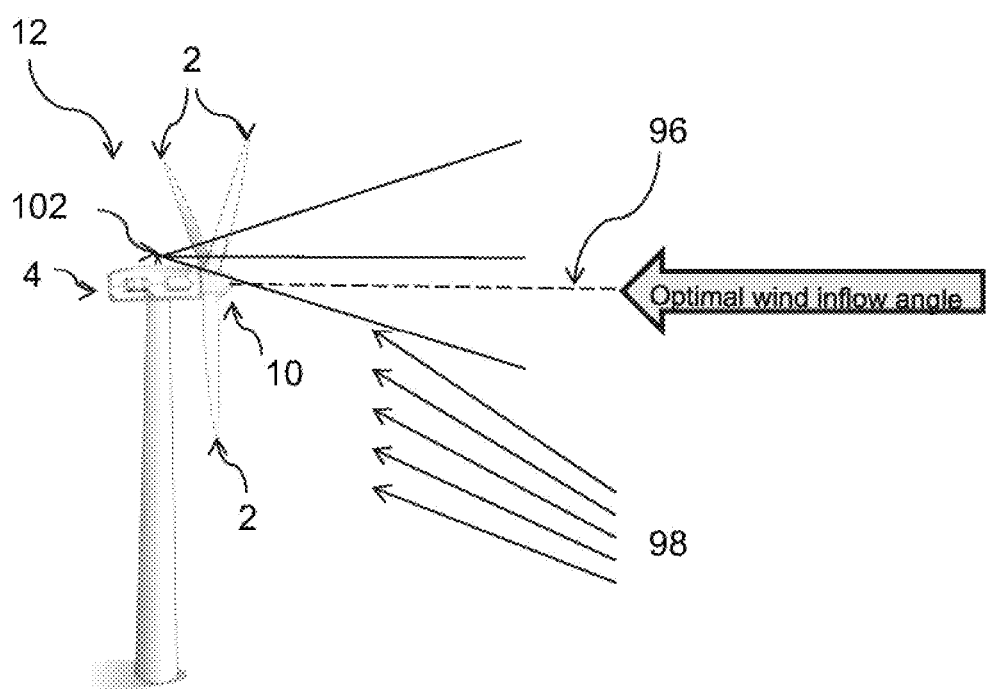

FIG. 18 shows an example of the function for the probability in relation to the wind speed (data measured in 1 m/s wind speed bins), FIG. 19A shows a plane view of a WTG 12 illustrating the actual sloped wind inflow measured by a LiDAR with circular scan pattern and the optimal wind inflow angle, FIG. 19B shows a plane view of a WTG illustrating the actual sloped wind inflow measured by a 4 beam LiDAR with linear scan pattern and the optimal wind inflow angle.

Figure 20A:
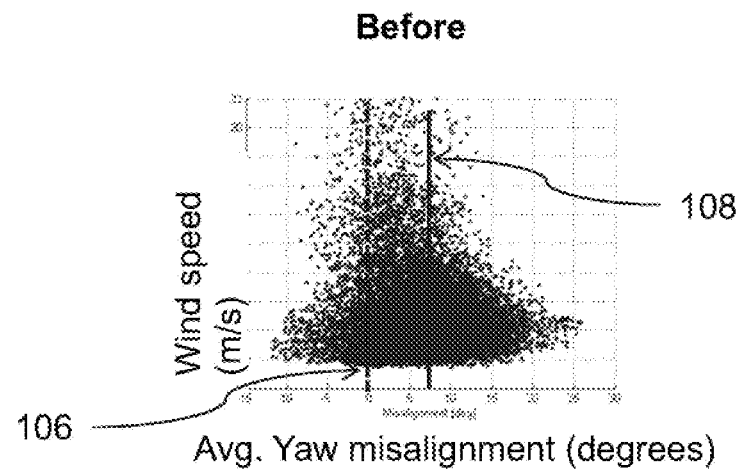
Figure 20B:
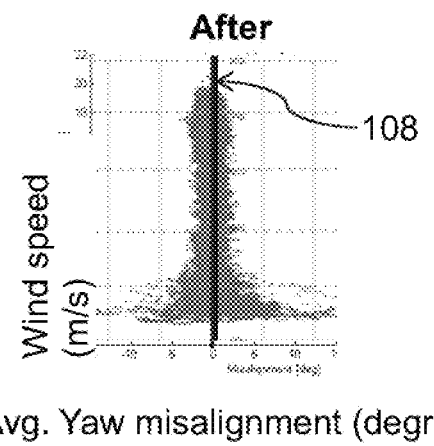
Figure 21:
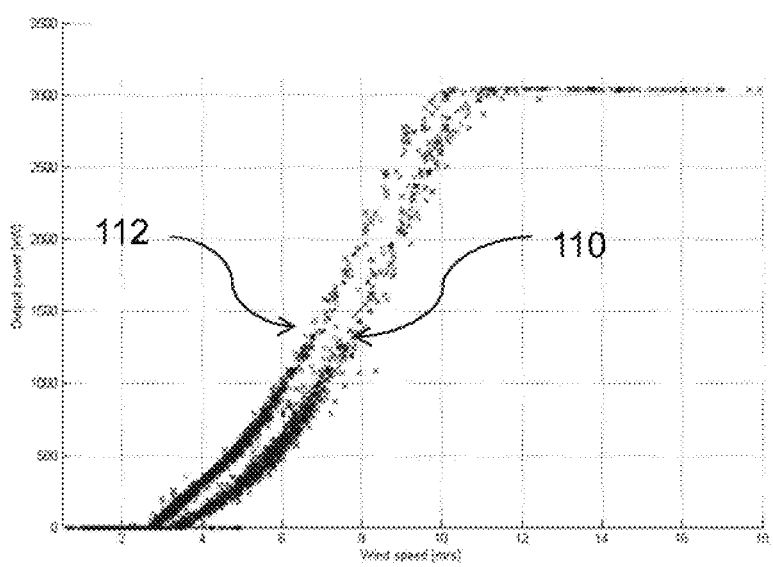

FIG. 20A shows a graphic presentation illustrating the actual yaw misalignment measurements related to wind speed before the installation and interconnection of a condition monitoring box system integrated with the WTG controller according to the present invention, FIG. 20B shows a graphic presentation illustrating the typical yaw misalignment measurements related to wind speed after the installation and interconnection of a condition monitoring box system with the permanently installed measure instruments and the WTG controller according to the present invention, and FIG. 21 shows a graphic presentation illustrating the actual power curve from a 3 MW WTG before and the typical power curve after the installation and interconnection of a condition monitoring box system with the permanently installed measure instruments and the WTG controller according to the present invention.

FIGS. 22A and 22B show a schematic overview of overall input and diagnostic of an example embodiment.

FIG. 22C shows examples on actions.

DETAILED DESCRIPTION OF THE INVENTION

Figure 1:
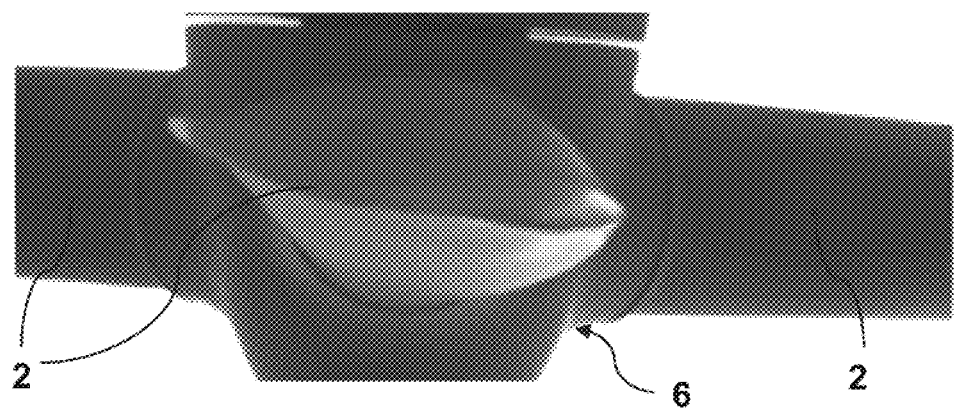
FIG. 1 shows a photographic image illustrating an expected camera view in this case when the camera is placed at the bottom of the tower and pointing towards the rotor blade tip.

FIG. 1 shows a photographic image illustrating an expected camera view—in this case when the camera is positioned at the bottom of the tower and pointing towards the rotor blade tip.

Figure 2:
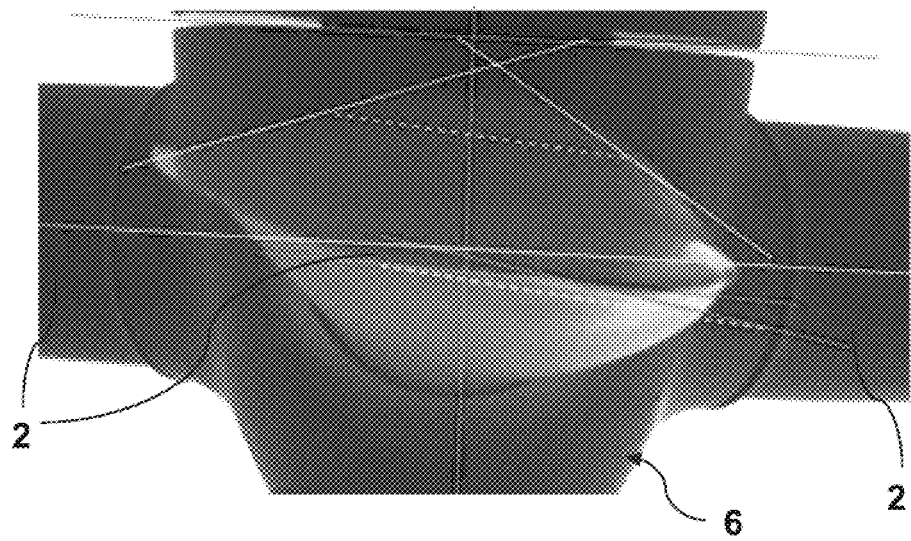
FIG. 2 shows a photographic image illustrating a rotor blade view with examples of measurement lines.

FIG. 2 shows a photographic image illustrating a rotor blade view—with examples of measuring lines (edge "helping lines" added to the image) provided by means of machine vision software so that it is possible to detect edges and shapes so that measurement, comparing and analysing becomes possible.

Figure 3A:
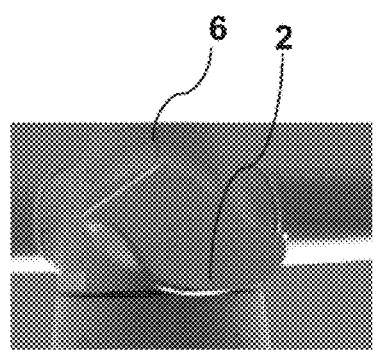
FIG. 3A-3C show photographic images captured with an area scan camera showing the same view for the three rotor blades.
Figure 3B:
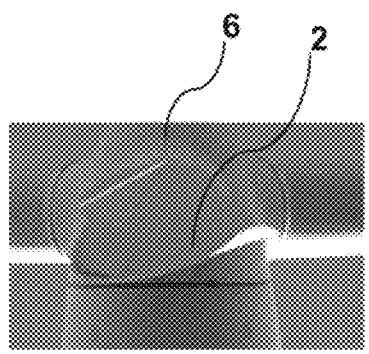
Figure 3C:
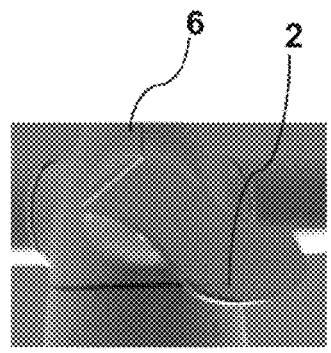

FIGS. 3A-3C show area scan images showing the same view for the three rotor blades including "helping lines" for measurement, comparison and analyze purposes.

Figure 4A:
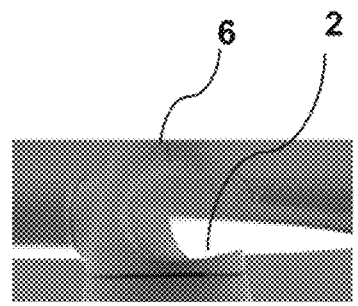
FIG. 4A-4C show photographic images captured with an area scan camera as consecutive images illustrating a very clear mutual displacement of the three rotor blades.
Figure 4B:
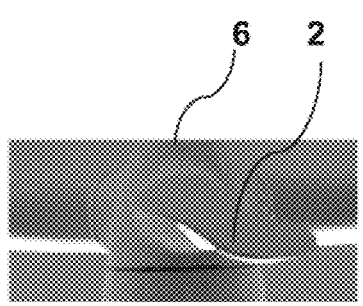
Figure 4C:
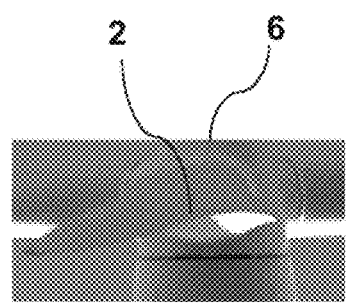

Area scan and line scan view are illustrated in FIG. 4A-4C to FIG. 5, that show different rotor blade views for inspiration of how and what to measure. In FIG. 4A-4C the motion is captured as consecutive images. The displacement is very clear.

Figure 5:
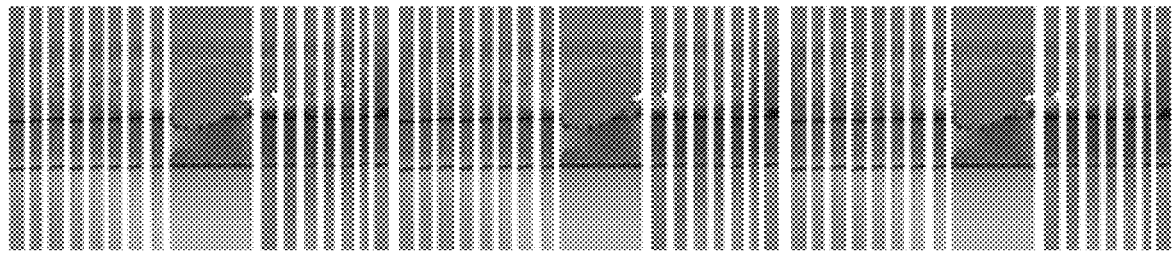
FIG. 5 shows photographic images captured with a line scan camera of all three rotor blades in one image (constructed from a 20 pictures/sec video)
Figure 6:
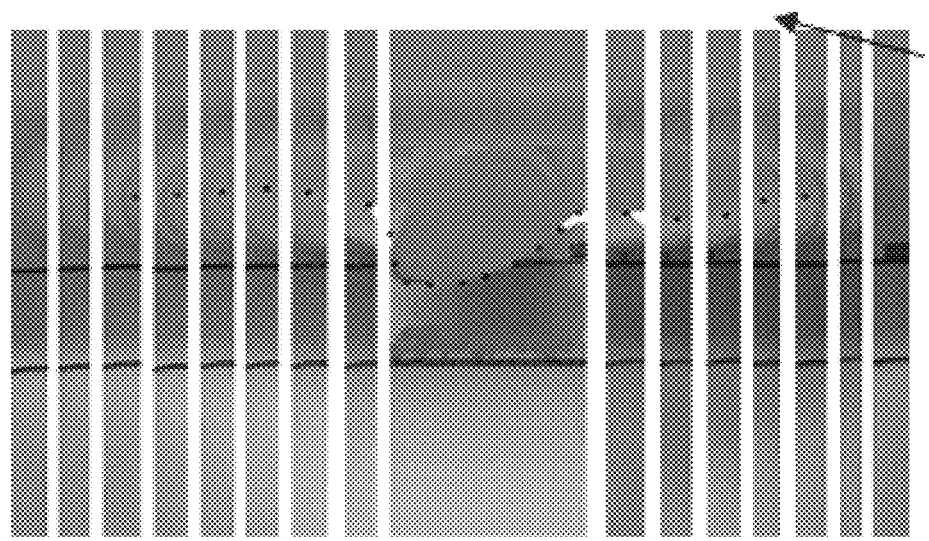
FIG. 6 shows photographic images captured with a line scan camera and illustrating one-blade images (constructed from a 20 pictures/sec video).

FIG. 5 shows photographic images captured with a line scan camera of all three rotor blades in one image (constructed from a 20 pictures/sec video). FIG. 6 shows photographic images captured with a line scan camera and illustrating one-blade images (constructed from a 20 pictures/sec video).

Line scan representation of motion: A running rotor is shown. The motion is captured as one "long" image (a full rotor turn). As far as known, there don't exist pictures of a turbine rotor captured with a line scan camera. The image in FIG. 6 is manually created out of a 20 picture/sec. video film. A line scan camera captures only one pixel/line, but to visualize, a small strip is taken from each picture in the film. The strips are assembled as shown in FIG. 6.

The specialty in the line scan captured picture is, that together with the blade tip we also get a clear picture of the blades—where the blade tip, the leading edge and the trailing edge, respectively, in FIG. 6 are marked with dots. Whereby it becomes easier to carry out a visual inspection of the individual blades for surface damages and measure all relevant parameters as pitch, bending, twisting etc.

Both thermographic, areas scan and line scan cameras can be used for blade inspection of all items on the rotor during rotation and full production.

Blade edge check: An example is damages after big stones hit the blade. (Stones can be lifted by wind/tornado)

Blade surface check: Many surface damages can be checked as open cracks, fiber damages and holes. These kinds of damages can be visualised directly or as shadows created by floodlight or laser light.

Camera view angle and camera position: The camera(s) can be placed in all positions in relation to capture images for analysis. It can be situated from below, the front side, rear side, edge sides and all around by using drones (Helicopters).

Tower stability analysis: Based on the images taken, the tower frequency, movement, tilt and twist during still stand, start up and during production can be analyzed.

Park analysis: The camera rig will be equipped with an electronic compass so the absolute rotor direction can be captured. Together with timestamp, wind speed measurements and analysis results statistical materials can be saved in a hard disk for every single blade in the park. Afterwards it will be possible to extract, sort and compare data.

Figure 7:
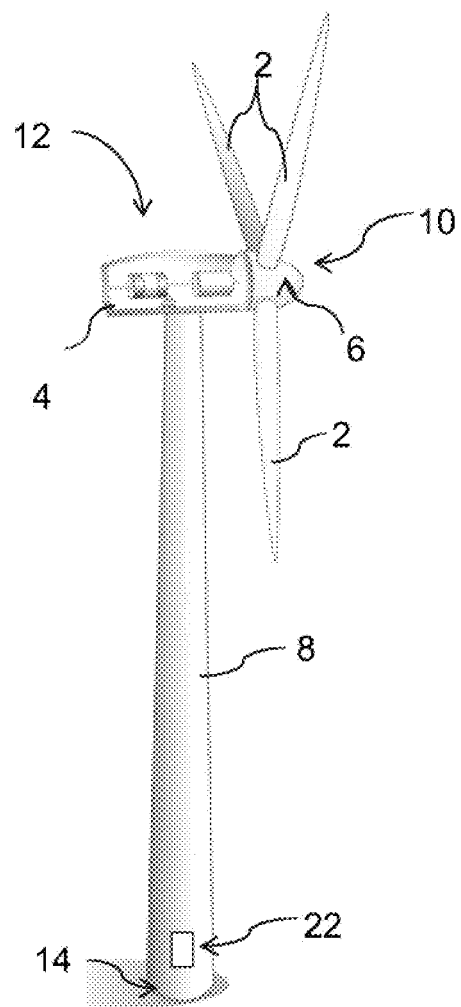
FIG. 7 shows a perspective view illustrating an embodiment of a WTG.

In FIG. 7 is shown an embodiment of a WTG 12 and its main components the nacelle 4, the blades 2, the hub/spinner 6, the rotor 10 (the rotor 10=spinner/hub 6+on which the rotor blades 2 is mounted), the tower 8, the foundation 14 and the WTG Controller 22.

Figure 8:
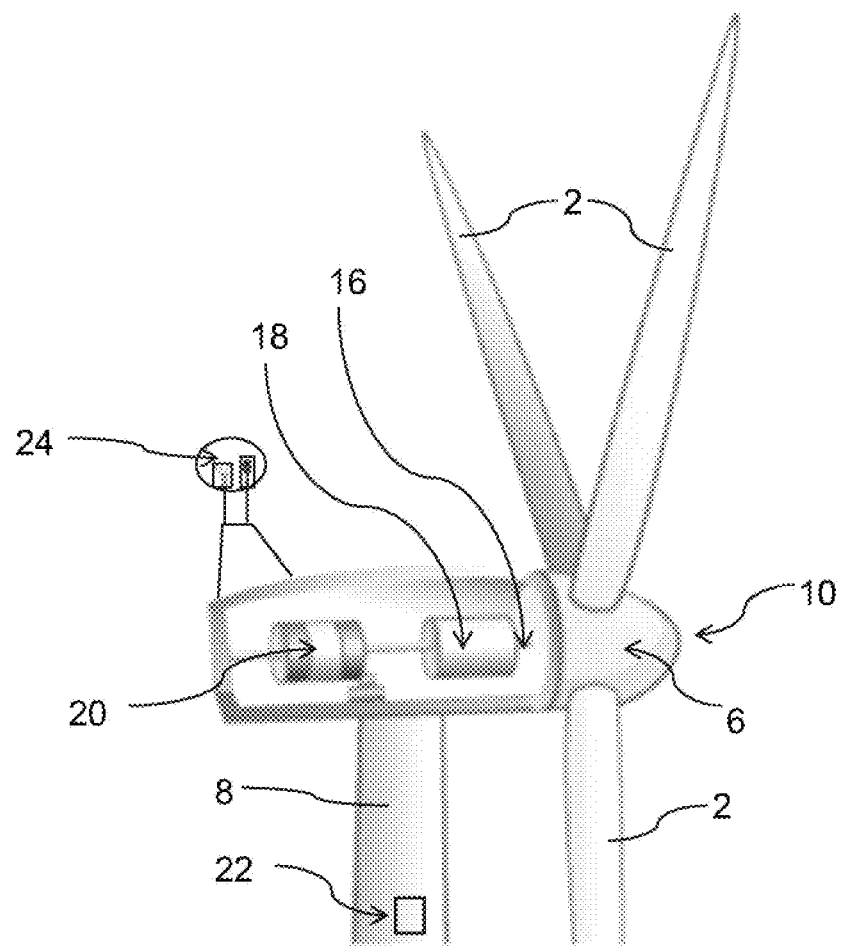
FIG. 8 shows a perspective view illustrating an embodiment of some of the main components in a WTG.

In FIG. 8 is shown an embodiment of a WTG 12 and its main components the blades 2, the hub/spinner 6, the rotor 10 (the rotor 10=spinner/hub 6+on which at least one rotor blade 2 is mounted), the tower 8 and the WTG Controller 22. Additionally is shown an embodiment of the main components in/on the nacelle 4, which is the main shaft 16, the gearbox 18, the generator 20 and the wind speed and wind direction measurement instruments 24.

Figure 9A:
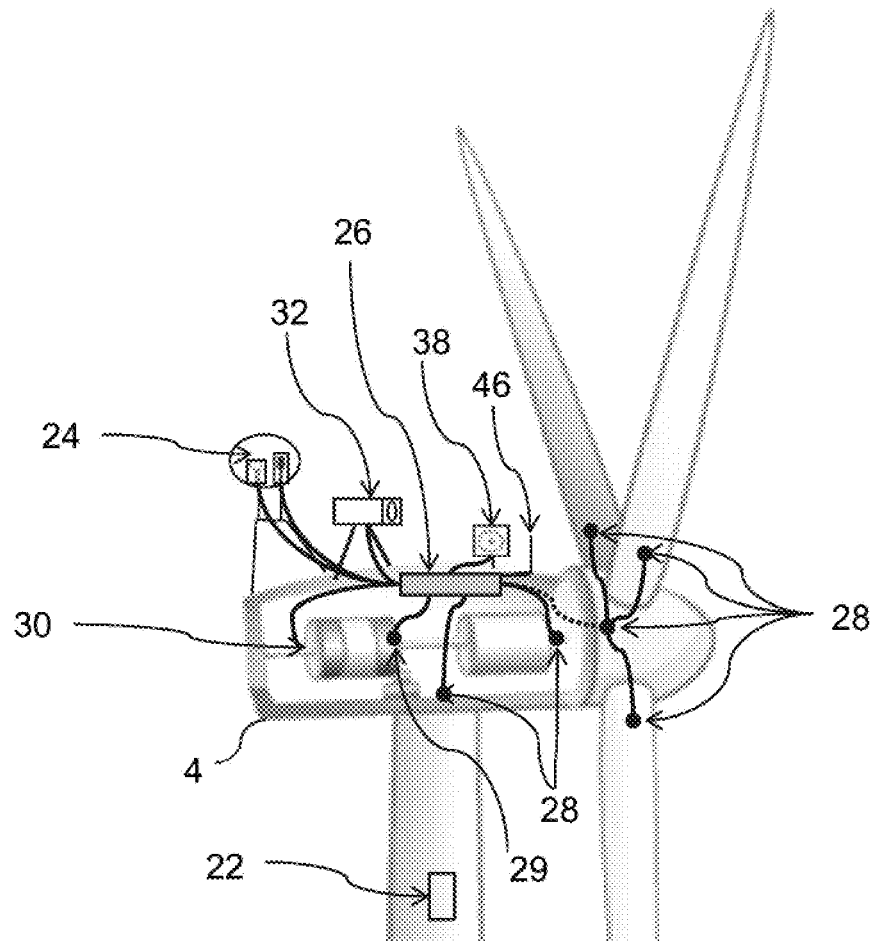
FIG. 9A shows a plane view of a preferred embodiment for the measuring arrangement for the collection and storage in a condition monitoring box of measurements from the stationary measurement equipment of a WTG as well as measurements collected by means of a temporarily or permanently installed LiDAR where the condition monitoring system is operating as a stand-alone installation.

In FIG. 9A is shown an embodiment of a typical measurement arrangement of a typical application environment for the invention "Method of condition monitoring of wind turbine fleets and individual wind turbines and parts thereof and perform instant alarm when needed". Here in FIG. 9A for the Condition monitoring box 26 operating independently of the WTG controller 22.

The Condition monitoring box 26 is shown located inside the nacelle 4. Further located inside the nacelle 4 is situated the accelerometers/sensors 28 located on the main shaft and in a position of the centre of the tower, and the torque measurement sensor 29, and the generator power production measurement sensor(s) 30 are situated on the generator power production cables from the generator.

On the rotor 10 the accelerometers/sensors 28 are located in the hub and on the individual blades.

On top of the nacelle 4, the antennas 38 for the GPS position, tilt and direction system, the antenna 46 for the satellite communication system, the existing meteorological sensors/instruments 24 and potentially also a LiDAR 32 is situated.

Figure 9B:
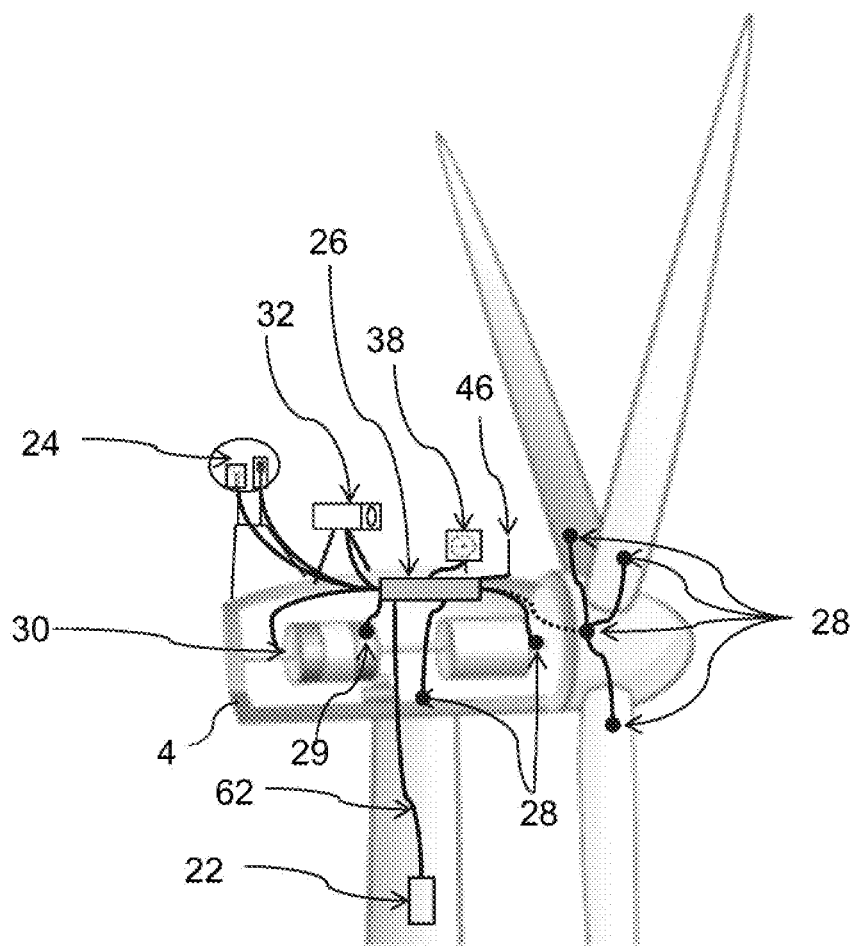
FIG. 9B shows a plane view of the afterwards situation of a preferred embodiment for the measuring arrangement for the collection and storage in a condition monitoring box of measurements from the stationary measurement equipment of a WTG where the WTG condition monitoring box is interconnected between the permanently installed measure instruments and the WTG controller.

In FIG. 9B is additional to FIG. 9A shown an example where the condition monitoring box 26 is interconnected between the permanently installed new and existing measurement instruments and the WTG controller 22 in such a manner that new and more precise input measurements received from the condition monitoring box 26 continuously will be provided to the WTG controller 22.

The new and more precise input measurements from the Condition monitoring box 26 will be calculated by making use of stored table values, technical methods and/or algorithms in the signal correction box 26 before the output is send to the WTG controller 22 this considering:

A. Time stamped generator power production measurements provided by the generator output measurement instruments 30, synchronized with
B. Time stamped and synchronized input from sensors 28 installed in the hub 6, on rotor blades 2, on main shaft 16 and in the nacelle 4 in the centre of the tower 8 providing position-dependent measurements of movements, accelerations, angles of rotation of the rotor, the individual rotor blades and the tower in x, y and z axes, synchronized with
C. Time stamped nacelle 360° actual wind direction measured by the permanently installed compass 11 (or the like), synchronized with
D. Time stamped wind measurements from existing measurement instruments and/or potentially also from temporarily installed measurement instruments
E. Time stamped measurement from torque sensor 29, The existing measurement instrument 24 will still be connected directly to the WTG controller 22, this assuring that any safety system of the WTG is intact.

Figure 10A:
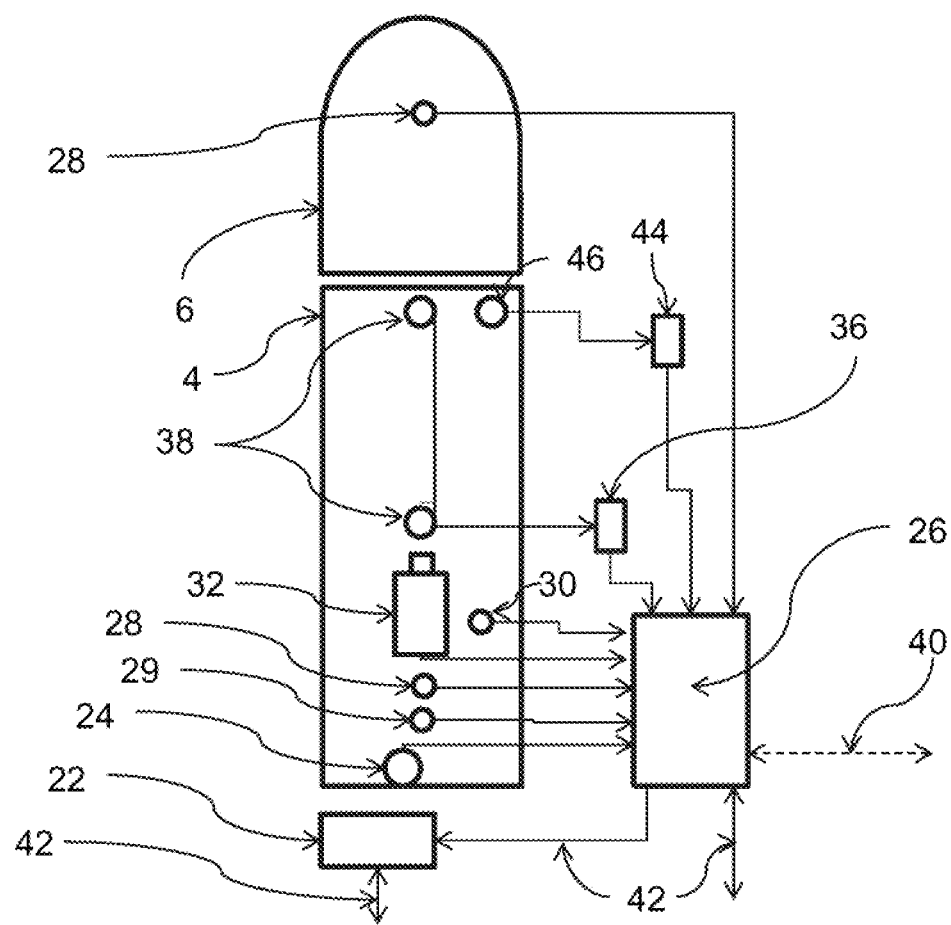
FIG. 10A shows a plane schematic system overview of a typical application environment for the condition monitoring box showing major components.

FIG. 10A shows an embodiment of a system overview of a typical application environment for the condition monitoring box 26 showing major components thereof where the nacelle 4, the rotor 10 and the WTG controller 22 are shown in the left hand side of the figure, while the condition monitoring box 26, GPS position, tilt and direction system 36, and the satellite based communication system 44 is shown to the right hand side of the figure.

On the rotor 10 the accelerometers/sensors 28 are located in the hub 6 and on the individual blades 2.

On top of the nacelle 4 is situated, the antenna 46 for the satellite communication system 44, the existing meteorological sensors/instruments 24, potentially also a LiDAR 32 and the antennas 38 for the GPS position, tilt and direction system 36. Said GPS antennas 38 are calibrated to the longitudinal axis defining the direction of the nacelle 4.

Inside the nacelle 4 is situated the condition monitoring box 26, the GPS position tilt and direction compass system 36, the satellite based communication system 44, the accelerometers/sensors 28 are located on the main shaft and in a position on top of the centre of the tower, and torque measurement sensor 29 and the generator power production measurement sensor(s) 30 are situated on the generator power production cables.

The condition monitoring box 26 receive signals from the meteorological sensors 24, potentially also from the LiDAR 32, from a precision GPS position tilt and direction compass system 36 (or the like), from the satellite based communication system 44, from the accelerometers/sensors 28, from the torque measurement sensor 29 and from the generator power production measurement sensor(s) 30.

Furthermore, the condition monitoring box 26 can receive signals from optional sensors 48 as indicated with a dotted interaction arrow 40.

The condition monitoring box 26 is receiving commands and providing instant alarm signals via satellite and offers data transfer options via GPRS/SMS/Satellite/Internet or other relevant communication system to owner/operator 68, mobile device 70 and local server 72 as indicated with a dotted interaction arrow 42.

The condition monitoring box 26 can also receive and provide signals and data to the WTG controller 22 as indicated with a dotted interaction arrow 42.

The WTG controller 22 furthermore may be interconnected with a user SCADA—as indicated by a double interaction arrow 42.

The permanently installed instruments related to the condition monitoring box 26 are manually and automatically calibrated when installed and if needed also in relevant time intervals which ideally will be synchronized with the change out of anemometers and wind vanes 24.

Figures 10B, 10C:
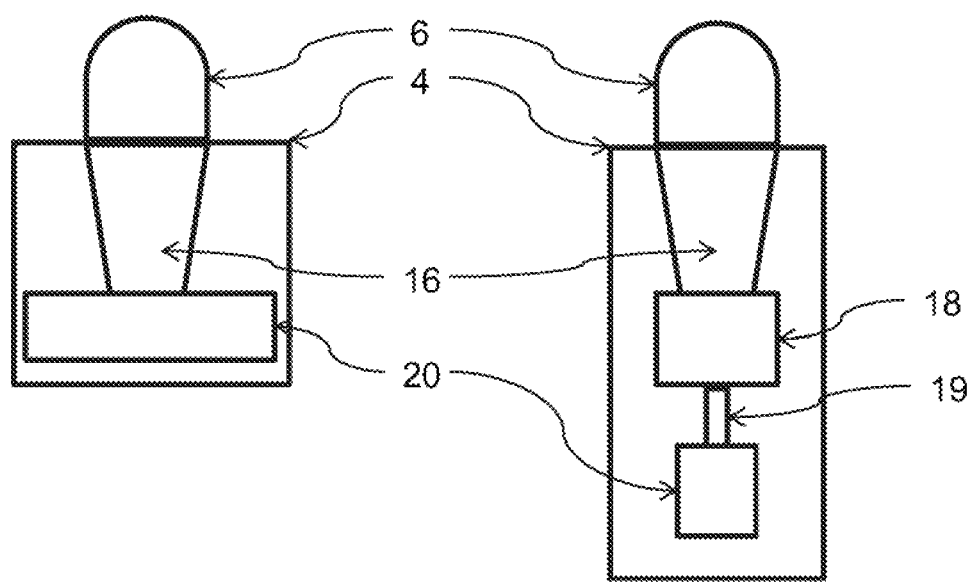
FIG. 10B shows a plane schematic view of further embodiments of WTG with a gearless drive train.
FIG. 10C shows a plane schematic view of further embodiments of WTG with traditional drive train.

FIG. 10B show plane schematic view of further embodiments of WTG with a gearless drive train 35 (hub/spinner 6, main rotor shaft 16 and generator 20) However, the nacelle 4 shown in FIG. 10B may as well represent a traditional WTG drive train 35 as shown in FIG. 10C.

FIG. 10C show plane schematic view of further embodiments of WTG with traditional drive train 35 (hub/spinner 6, main rotor shaft 16, gear box 18, high speed shaft 19 and generator 20)

Figure 11:
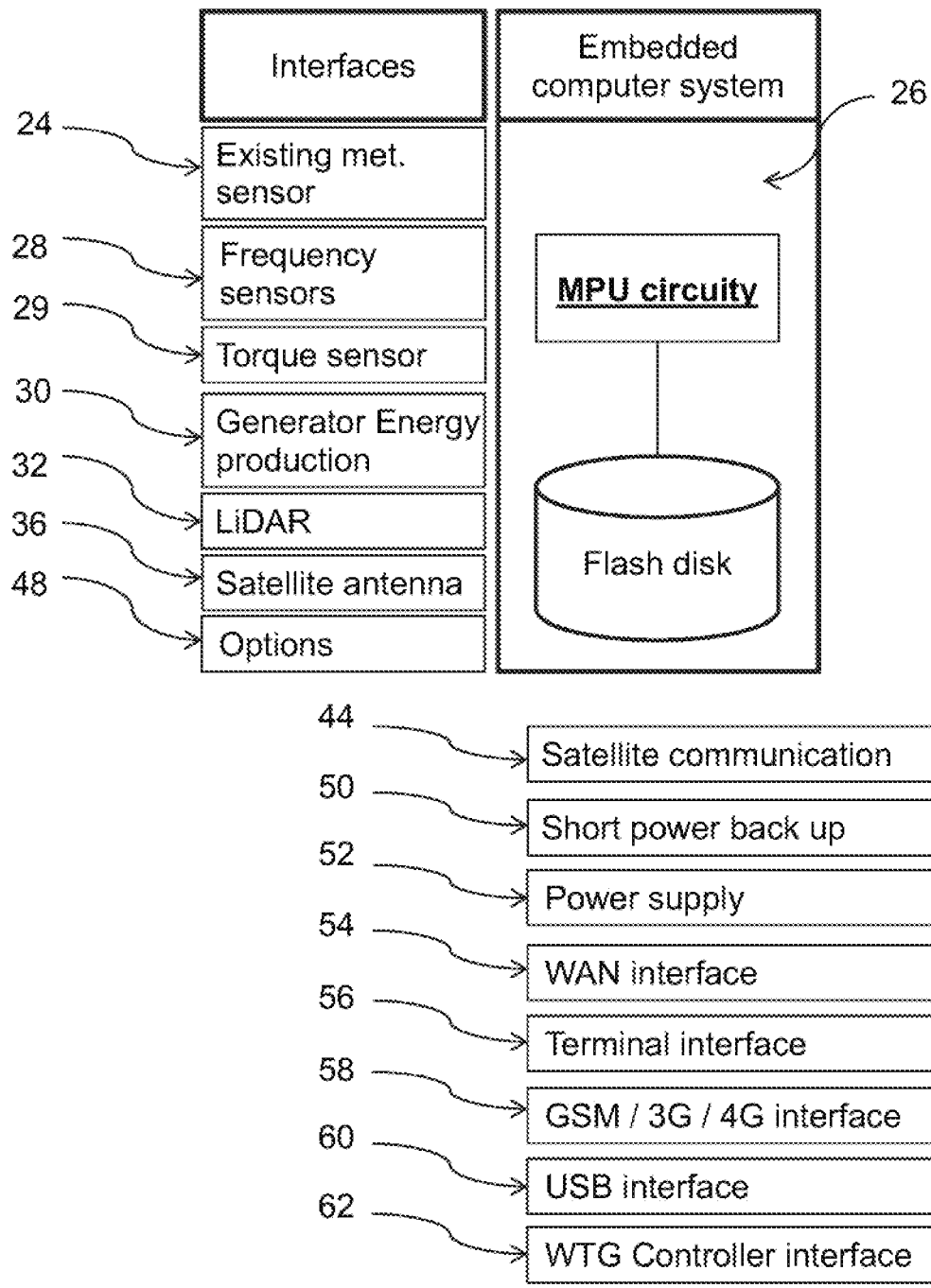
FIG. 11 shows a top-level typical hardware implementation view of the condition monitoring box.

FIG. 11 shows an embodiment of a typical hard ware implementation of the condition monitoring box 26, where on the left side is shown the interfaces relating to:

24—at least receiving input from one existing measurement instruments located behind the rotor providing at least input about actual meteorological conditions behind the rotor by use of measurements of wind speed and potentially also wind direction measurements.

28—at least one accelerometer and sensors installed in the hub, on each of the rotor blades, on the main shaft and in the nacelle located in the centre of the tower providing position-dependent measurements of movements, accelerations, angles of rotation of the rotor, the individual rotor blades and the tower in x, y and z axes. All these sensors should be synchronized.

29—at least one torque measurement sensor measuring torque on the generator 20,

30—at least one power measurement device providing measurements of instantaneous generator power production values.

36—at least one permanently installed nacelle/drivetrain direction measurement instrument (compass or the like) for precisely measuring the nacelle/drivetrain direction enabling comparison with the input measurements related to the actual nacelle direction—and provide information about when the nacelle yaw system actually are turning the nacelle to be able to evaluate the change in the aerodynamic efficiency of the rotor.

32—optional input about actual meteorological conditions from nacelle mounted LiDAR, spinner anemometer or other instruments measuring wind speed, turbulence and potentially also wind direction and wind inflow angle etc. in front of the rotor and takes into account said stored input about atmospheric conditions obtained by these sensing means, and

48—optional input from additional relevant condition monitoring and measurement instruments which can be added to extend the invention to support a Critical Component Condition Monitoring, Fault Detection and Instant Alarm System for other key components in a WTG and parts thereof, and FIG. 11 where in the centre is shown the condition monitoring box 26 with at least one processor for processing said input. There is at least one storage means for the storing of collected measured and calculated values etc. to be used as reference table for technical methods, multi-dimensional algorithms and other technologies for the establishment of regulatory output.

FIG. 11 while in the right hand side of the figure is shown the output interfaces relating to:

44—at least one reliable communication and time synchronization system interconnected with satellite antenna 46, or any other communication interface that may become relevant in the future, providing and receiving an instant alarm message and other information to/from the owner/operator/24/7 surveillance centers for appropriate action. Additional the time setting provided by the communication channel is used for setting time synchronization in the condition monitoring box software on an adequate frequent basis to synchronize time setting in all signal correction boxes on a wind turbine fleet basis.

50—at least one power backup with sufficient capacity to safely shut down all software in the condition monitoring box 26 and attached systems in case of sudden loss of permanent power supply.

52—at least one power supply to the condition monitoring box and attached systems.

56—at least one terminal interface and one USB interface option.

60—and at least one communication interface providing option to transfer larger data amounts—could be WAN interface 54 or GPRS/3G/4G/5G interface option 58, or any other communication interface that may become relevant in the future to be able to transfer larger data amounts to the owner/operator/24/7 surveillance centers for appropriate action, and 62—at least one permanent on line connection option from the said condition monitoring box 26 to the WTG controller 22 to interconnect and transfer a regulatory output to the WTG controller 22 and potentially also to receive input from the WTG controller 22.

Figure 12:
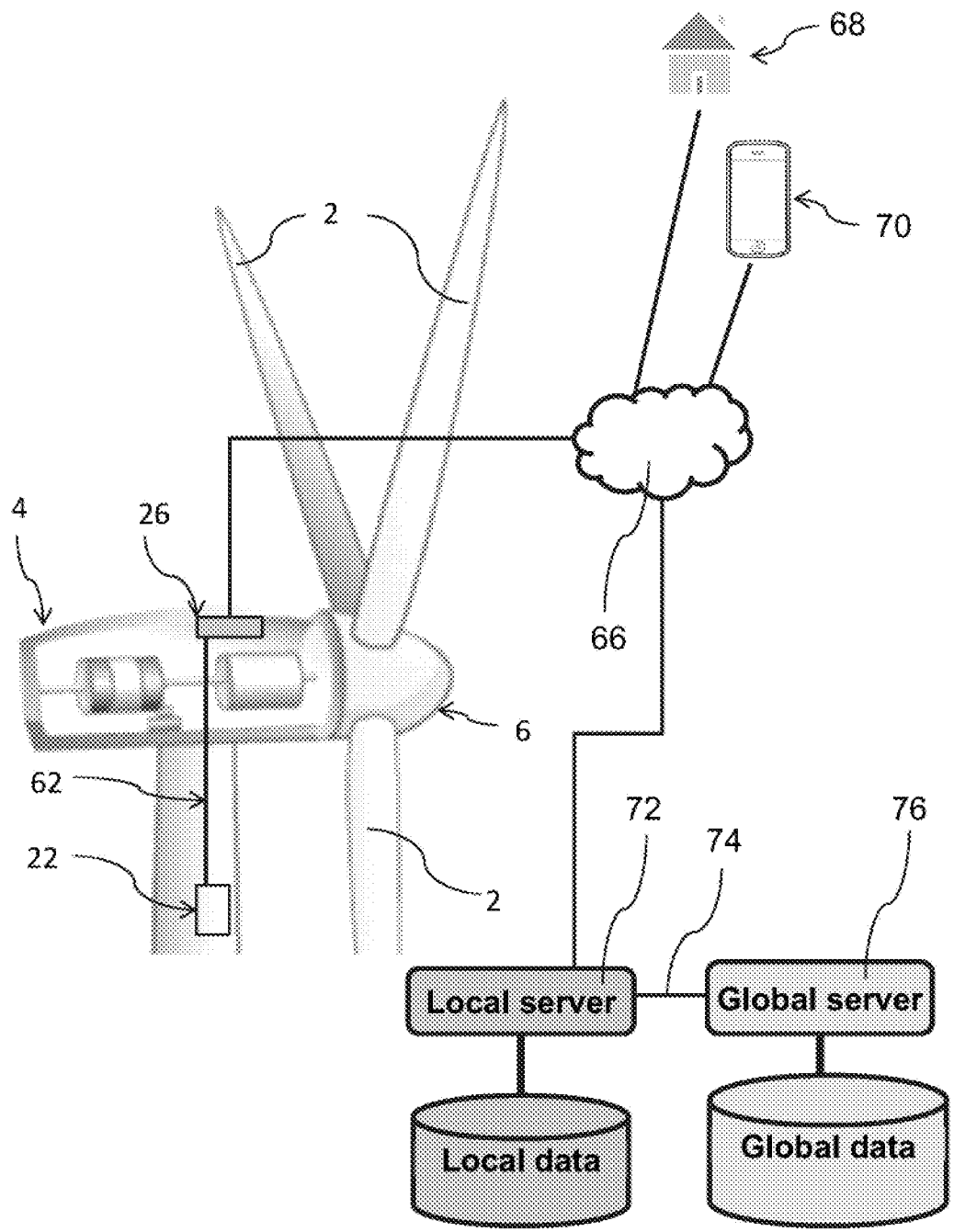
FIG. 12 shows a top-level typical data transfer and communication lines implementation view of the condition monitoring box, where the WTG condition monitoring box is interconnected between the permanently installed measure instruments and the WTG controller.

In FIG. 12 is shown an embodiment of a data transfer and communication arrangement of a typical application environment for the invention "Method of condition monitoring of wind turbine fleets and individual wind turbines and parts thereof and perform instant alarm when needed". The condition monitoring box 26 is interconnected with the WTG Controller 22 illustrated by line 64. The condition monitoring box 26 will also provide instant alarm and receive WTG stop signals etc. via satellite or any other communication interface that may become relevant in the future to be able to transfer these signals to the owner, operator 68, 70 and to server in 24/7 local surveillance center 72 illustrated by line and cloud 66. The condition monitoring box 26 will furthermore offer data transfer options via GPRS/3G/4G/SMS/satellite/internet or any other communication interface that may become relevant in the future to be able to transfer larger data amounts illustrated by line and cloud 66 from the condition monitoring box 26 to the owner, operator 68, 70 and to server in 24/7 local surveillance center 72 where data can be stored for further analysis and statistics. Instant alarm and data will also be transferred using internet 74 from local server 72 to a global server 76 where it will be stored for further analysis and statistics.

In the longer term a server in a local/regional surveillance center 72 or a server in a global and logistic surveillance center 76 will monitor and collect data from all the condition monitoring boxes 26 located in the nacelle 4 in agreed sequence and will be able to remotely transfer back signals, commands, algorithms, updated software etc. to the condition monitoring box 26 installed in nacelle 4 or directly to the WTG controller 22 or directly to the owner and operator 68, 70.

Figure 13:
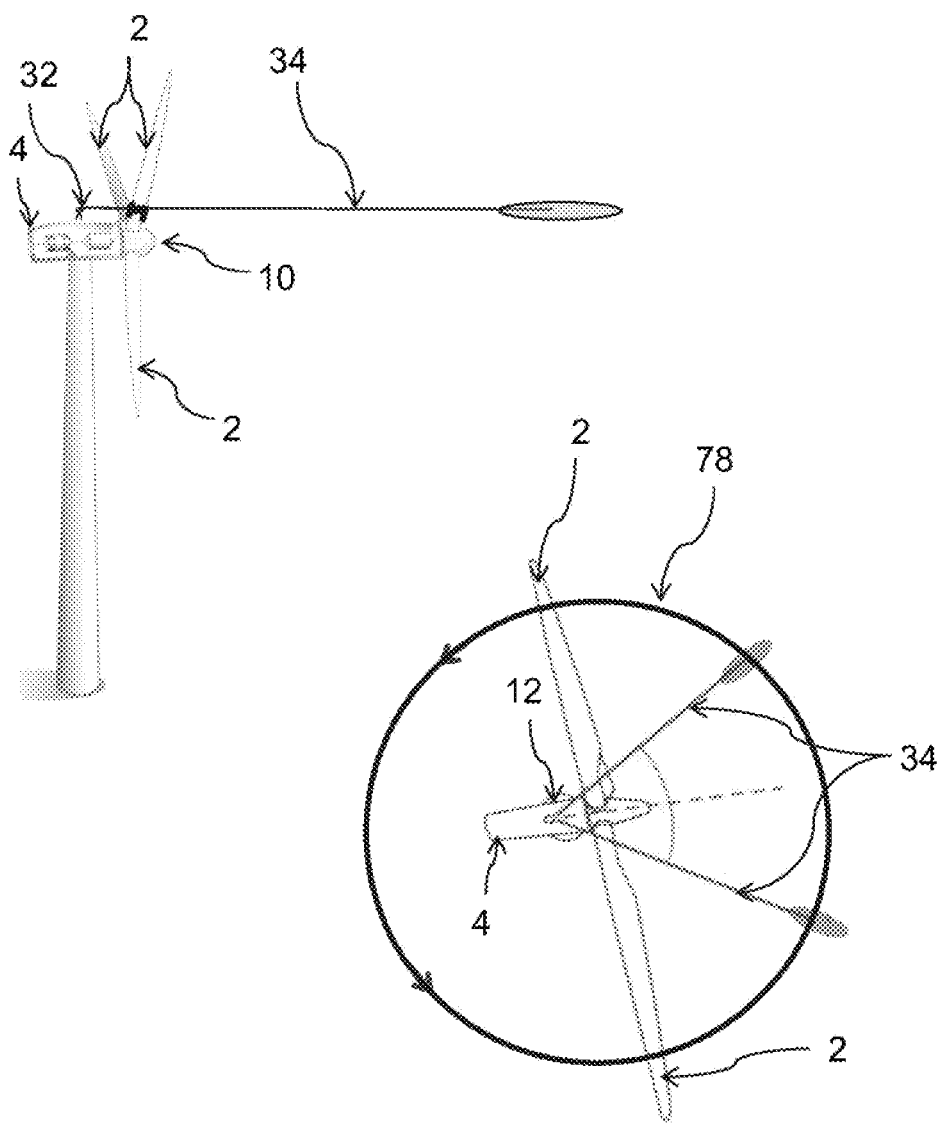
FIG. 13 shows a plane view illustrating a 2 beam LiDAR temporarily collection of wind speed, yaw misalignment, turbulence and wind inflow angle etc. in front of the rotor measurements representing measurements from 360° wind sectors surrounding the WTG.

FIG. 13 serves to illustrate the optional collection and storage of more precise measurement of wind conditions—wind speed, wind direction, and potentially also turbulences and wind inflow angle in this case said using a nacelle based LiDAR 32 measuring in a distance of some 70-80 meters in front of the rotor 10 with one or more laser beams 34—as indicated with an arrow 78—these precise measurements are carried out in a 360° radius surrounding the WTG 12.

This collection of wind condition values may be completed through more days or weeks before the necessary measurements from the most dominating surrounding wind sectors and/or wind speed bins are collected and stored in the condition monitoring box 26.

Special geographic or local conditions can make it impossible to collect measurements from all wind bins and wind sectors surrounding the WTG 12—however in case of missing wind bins and/or wind sector measurements from specific wind sectors such measurements may be substituted by measured or extrapolated wind condition values.

By the collection of LiDAR generated measurements one may be aware of the general mode of operation of a LiDAR using laser beams to measure reflections from air particles in the atmospheric air in front of the rotor 10.

This means that under certain conditions e.g. heavy fog or rain the LiDAR will not be able to measure any reflections from air particles in front of the rotor 10.

Figure 14A:
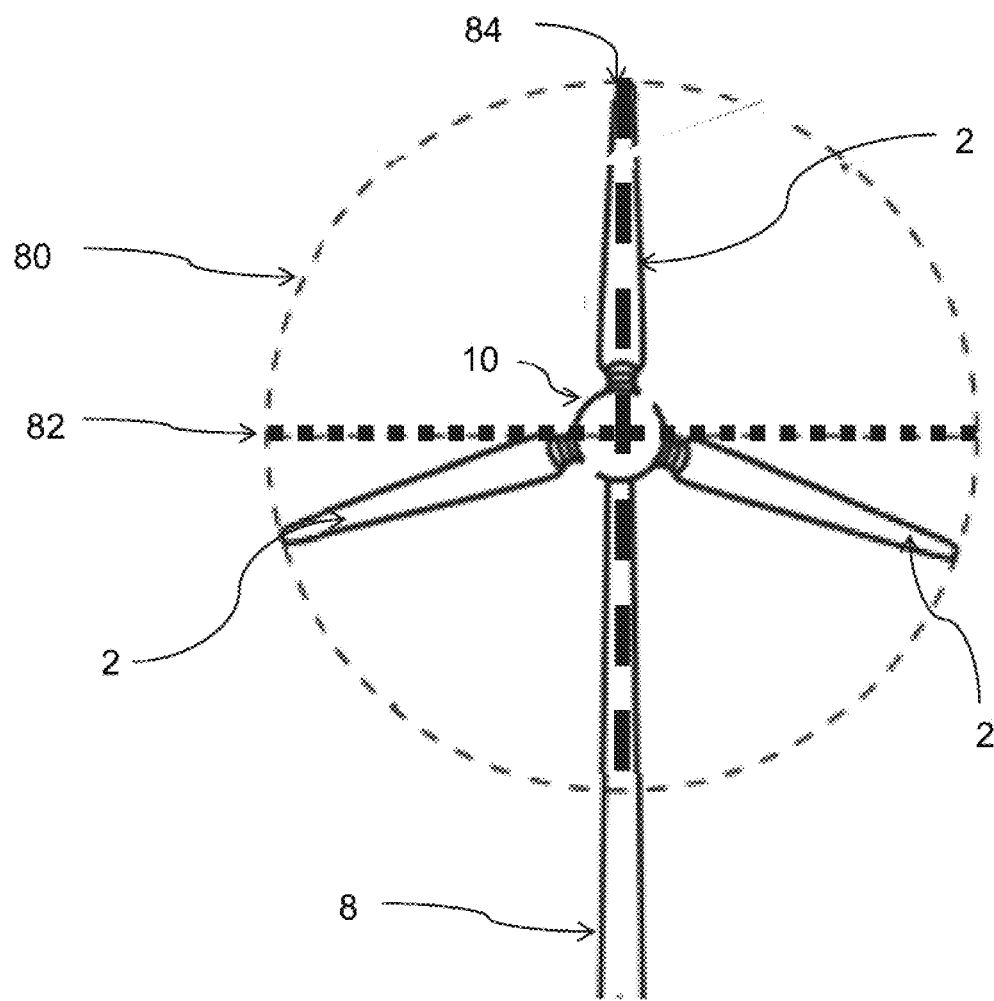
FIG. 14A shows a plane view of the rotor and the tower of a wind turbine with a circle illustrating the swept area by the rotor, with dotted line illustrating the horizontal direction (with respect to rotor plane) and with dotted line illustrating the tangential direction (with respect to rotor plane). These terms are normally used when discussing the "Blocking effect in front of the rotor" and the "Wake effect behind the rotor"

FIG. 14A shows an embodiment of a WTG 12 with its tower 8 and three blades 2 and a dotted circle to illustrate the swept area 80 by the rotor 10, a dotted line to illustrate the horizontal direction (with respect to rotor plane) 82 and a dotted line to illustrate the tangential direction (with respect to rotor plane) 84.

Figure 14B:
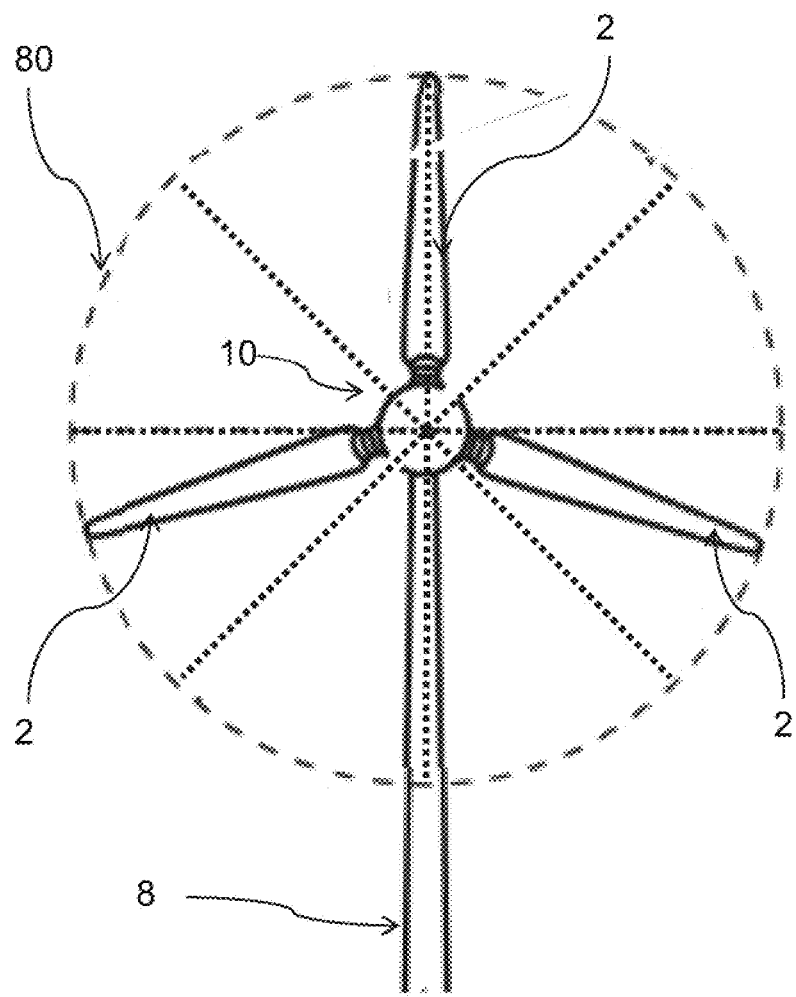
FIG. 14B shows an example where the area swept by the rotor is divided into eight equally sized sectors of each 45° by four dotted lines.

FIG. 14B shows an example where the swept area 80 is divided into eight equally sized sectors of each 45° by four dotted lines—but any other division of the area 80 swept by the rotor into equally sized sectors may be relevant.

The entire rotor's 10 aerodynamic efficiency for the 360° swept area 80 by the rotor can be quantified by the measured accumulated generator power production in the time period when a specific blade has rotated 360°.

An aerodynamic efficiency of a specific blade 2 in a specific sector of the area 80 swept by the rotor can be quantified by the measured accumulated generator power production in the time period where this specific blade 2 is located in the specific sector of the swept area 80.

Figure 15:
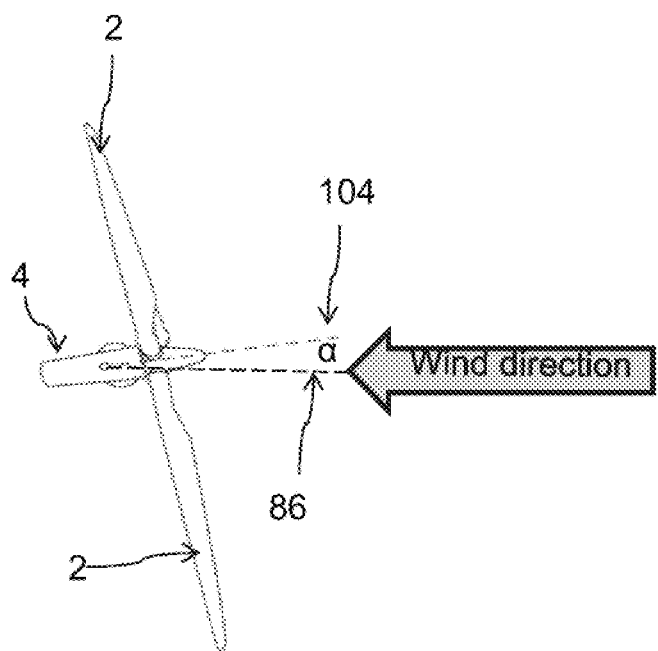
FIG. 15 shows a plane top view illustrating the yaw misalignment angle α between the wind direction and the real nacelle/drive train direction.

FIG. 15 serves to illustrate the misalignment angle α between the wind direction marked by an arrow 86 and the real nacelle/drive train direction marked by a dotted line 104. It should be emphasized that according to a common and well known issue the consequence from yaw misalignment is power loss following a $cos^2$ function and increased loads. Statistics show that 80% of random chosen WTG's operates with average yaw misalignment >2° and 50% of these WTG's operated with average yaw misalignment >6° and up to 30° leading to large yearly generator power production losses and increased loads.

Figure 16A:
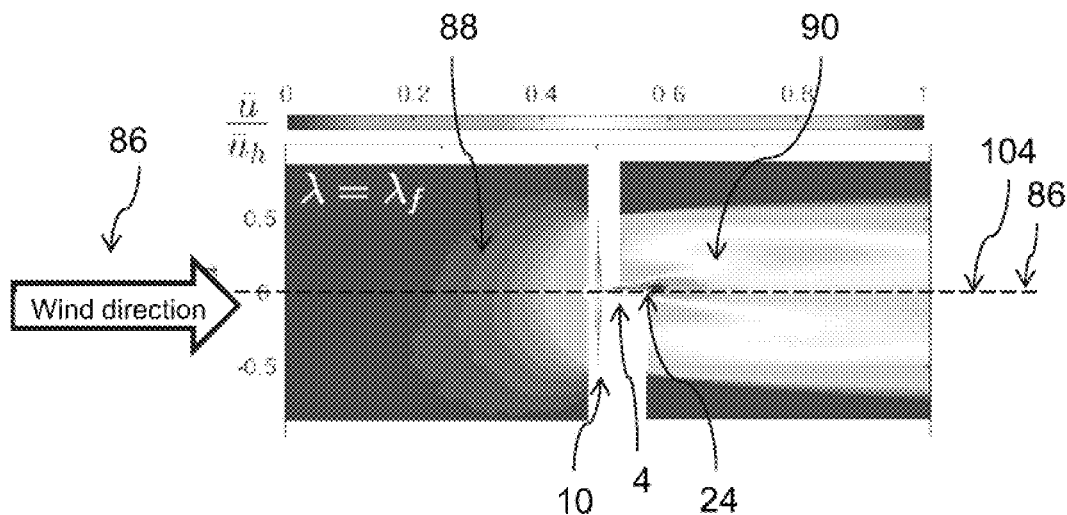
FIG. 16A shows copy of FIG. 5 presented at Wake conference 2015—Journal of Physics: Conference Series 625 (2015) 012014. From this image can be seen the rotor, the nacelle, the location of the existing measurement instruments together with the contours of the normalized mean stream wise velocity ($u/u_h$) in the horizontal plane (with respect to rotor plane) at hub height in the vicinity of the zero-yawed turbine. The contours of the buffer zone can be seen to the left in front of the rotor and the contours of the wake can be seen to the right behind the rotor. The wind direction is also indicated.

FIG. 16A shows a photographic image illustrating the blocking zone contours 88 to the left of the rotor 10 and the wake contours 90 to the right of the rotor 10 by the normalized mean stream wise velocity ($u/u_h$) in the horizontal plane 82 (with respect to rotor plane) at hub 6 height in the vicinity of the zero-yawed turbine (Wake conference 2015—Journal of Physics: Conference Series 625 (2015) 012014 FIG. 5.).

In the left hand side of FIG. 16A the wind direction arrow and line 86 illustrates the wind direction from where the wind is approaching the rotor 10. It can clearly be seen from the nacelle/drive train direction 104 that the yaw misalignment is 0°. It can clearly be seen from the wake contours 90 behind (to the right) the rotor 10 that the "wake" is not symmetrical exactly on the location where the existing measuring instruments 24 normally are located on the nacelle 4 which is one of the explanations why these instruments 24 cannot measure correctly from where the wind is approaching the rotor.

It can also clearly be seen from the blocking effect contours 88 in front (to the left) of the rotor 10 that the "blocking effect" in the horizontal plane 82 (with respect to rotor plane) at hub 6 height in front of the rotor 10 is not symmetrical primarily due to rotor rotation.

Figure 16B:
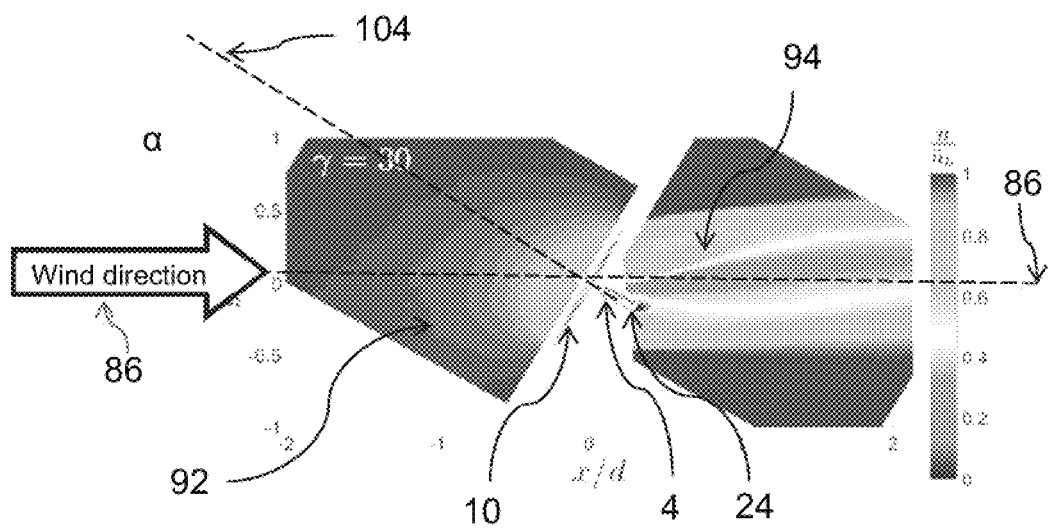
FIG. 16B shows copy of FIG. 12 presented at Wake conference 2015—Journal of Physics: Conference Series 625 (2015) 012014. From this image can be seen the rotor, the nacelle, the location of the existing measurement instruments together with the contours of the normalized mean stream wise velocity ($u/u_h$) in the horizontal plane (with respect to rotor plane) at hub height in the vicinity of the turbine operating with 30° yaw misalignment angle. The contours of buffer zone can be seen to the left in front of the rotor and the contours of the wake can be seen to the right behind the rotor. The yaw misalignment angle of α=30° between the wind direction and the real nacelle direction can also be seen.

FIG. 16B shows a photographic image illustrating the blocking zone contours 88 to the left of the rotor 10 and the wake contours 90 to the right of the rotor 10 of the normalized mean stream wise velocity (u/u$_h$) in the horizontal plane 82 (with respect to rotor plane) at hub 6 height in the vicinity of the turbine operating with 30° yaw misalignment angle (Wake conference 2015—Journal of Physics: Conference Series 625 (2015) 012014 FIG. 12).

In the left hand side of FIG. 16B the wind direction is marked by an arrow and line 86 and the real drive train/nacelle direction is marked by a dotted line 104 to illustrate the actual yaw misalignment angle α of 30°. It can clearly be seen from the contours 94 behind/to the right of the rotor 10 that the "wake" is not symmetrical in the horizontal plane 82 (with respect to rotor plane) at hub 6 height where the existing measuring instruments 24 normally are located on the nacelle 4 which is one of the explanations why these instruments cannot measure correctly where from the wind is approaching the rotor 10. By comparing FIG. 16A and FIG. 16B, it can also be seen that the "wake effect" in the horizontal plane 82 (with respect to rotor plane) at hub 6 height behind the rotor 10 is significantly more asymmetrically when the rotor 10 is operating with a 30° yaw misalignment.

It can also clearly be seen to the left side from the contours 92 in front of the rotor 10 that the "blocking effect" in the horizontal plane 82 (with respect to rotor plane) at hub 6 height in front of the rotor 10 is not symmetrical. By comparing FIG. 16A and FIG. 16B, it can also be seen that the "blocking effect" in the horizontal plane 82 at hub 6 height in front of the rotor 10 is significantly more asymmetrically when the rotor 10 is operating with a 30° yaw misalignment.

FIG. 17A shows in an photographic image how this invention expect the blocking zone contours 118 of the normalized mean stream wise velocity (u/u$_h$) in the tangential directions (with respect to rotor plane) 84 in front of the rotor 10 in the vicinity of the turbine operating with 0° yaw misalignment angle and operating with the same relative blade pitch angle. The expected contours of the buffer zone 118 can be seen in front of the rotor 10. The tilt angle of mounting for the rotor 10 (horizontally) with respect to the tower 8 ∈ is shown with the normal 7° tilt angle between the wind inflow direction in the optimal horizontal plane 96 and the real rotor 10 tilted direction 120 where the rotor 10 lean in a 7° angle ∈ away from the tower 8 to avoid strikes and coalitions.

FIG. 17B serves to illustrate additional to FIG. 17A the normal relation in relative wind speed in the tangential direction 84 (with respect to rotor plane). It can be seen that under normal conditions when the wind is approaching the rotor 10 in the optimal wind inflow angle 96, then the relative wind speed in the top position of the swept area of the rotor 114 is higher than the wind speed in the bottom position of the swept area of the rotor 116 which is illustrated by the length of the dotted wind speed arrows 122.

It can clearly be seen from FIG. 17A and FIG. 17B that the contours of the blocking zone 118 in front of the rotor 10 in the tangential directions (with respect to rotor plane) 84 in front of the rotor 10 is expected not to be symmetrical, primarily due to the wind speed is considerably higher in the top of the rotor 114 compared to the wind speed in the bottom of the rotor 116 which can be seen in FIG. 17B and secondarily also due to the 7° tilt angle of mounting for the rotor 10 (horizontally) and due to the rotation of the rotor 10.

Based on these findings related to the contours of the blocking zone in front of the rotor 10 (see 88 in FIG. 16A with a rotor 10 operating with 0° yaw misalignment) both in the horizontal direction 82 (with respect to rotor plane) and also the expected blocking zone in front of the rotor 10 (see 118 in FIG. 17A with a rotor 10 operating with 0° yaw misalignment) in the tangential direction 84 (with respect to rotor plane) it is therefore suggested in this invention that:

A. a rotor 10 has to operate with some average yaw misalignment (to be defined and included in the algorithms) to assure a symmetrical distributed blocking zone in front of the rotor 10 in the horizontal direction 82 (with respect to rotor plane) at hub height 6, which then will lead to maximum generator power production and minimum loads on the entire rotor 10 (primarily due to the same aerodynamic efficiency and balance of the individual blades 2 when positioned in the left side and the right side of the swept area 80 in the horizontal direction 82 (with respect to rotor plane) by the rotor 10).

B. for a rotor 10 operating with large yaw misalignment the aerodynamic efficiency and balance of the specific individual blade 2 in the horizontal direction 82 (with respect to rotor plane) at hub height 6 in front of the rotor 10 is considerably different when the individual blade 2 is positioned in the left side of the swept area 80 by the rotor 10 and when the same individual blade 2 is positioned in the right side of the swept area 80 of the rotor 10.

C. For a rotor 10 with the option to pitch the blades 2 individually on each turn of the rotor 10. When such a rotor 10 is operating with 0° yaw misalignment and when the wind is approaching the rotor 10 in the optimal wind inflow angle 96, then there should ideally be a relative differences in the actual blade pitch angles from when the individual blade 2 is located in the top position of the swept area 80 by the rotor 10 (114 in FIG. 17B) compared with when the individual blade 2 is located in the bottom position of the swept area 80 by the rotor (116 in FIG. 17B), this to assure a symmetrical distributed blocking zone in the tangential direction 84 (with respect to rotor plane) which then will lead to maximum generator power production and minimum loads on the entire rotor 10.

D. for a rotor 10 operating with 0° yaw misalignment and without the option to individually pitch the blades 2 on each turn of the rotor 10 any relative difference in between the actual pitch angles on the individual blades 2 is expected to have an effect on the symmetry of the contours of the blocking zone in the horizontal direction 82 (with respect to rotor plane) in front of the rotor 10 (88 in FIG. 16A and 92 in FIG. 16B) and also in the symmetry of the contours of the blocking zone in the tangential direction 84 (with respect to rotor plane) in front of the rotor 10 (118 in FIG. 17A). This type of rotor 10 has therefore ideally to operate without blade 2 pitch misalignment above 0.2° relatively in between the individual blades 2 to assure a best possible symmetrical distributed blocking zone in both the horizontal direction 82 and in the tangential directions 84 (with respect to rotor plane) in front of the rotor 10, which then is expected to lead to maximum generator power production and minimum loads on the entire rotor.

The present invention therefore provides a highly desirable better and totally new combined technology for condition measuring and monitoring the actual aerodynamic efficiency of the individual blades and the entire rotor in any 360° blade and 360° rotor position at any time during operation—to provide correct information to the wind turbine controller for obtaining the best possible generator power production and lowest loads to be within the specifications.

The invention suggest to use a combined technology to measure the aerodynamic efficiency of the individual blade and the entire rotor in any 360° position In this way a WTG can also use the entire rotor as a new innovative measuring instrument which the wind turbine industry have been looking for so many years now.

This new combined technology can support and eventually substitute the existing instruments located behind the rotor.

FIG. 18 shows a histogram and Weibull function for the probability in relation to the winds speed (data measured in 1 m/s wind speed bins).

Wind speed bin is the expression for a wind speed interval, typically 0.5-1 m/s. Wind speed data are grouped In each of these wind speed intervals (wind speed bins) and based on this relevant statistic's and calculations can then be made for each wind speed bin. This type of statistics and calculations can for example be power performance measurements and Weibull wind speed distributions like in figure below, where variations in wind speed are expected.

The reason why wind speed data are grouped in wind speed bins is that statistically variances are expected which is easier to analyze when data are grouped in those wind speed bins.

FIG. 19A serves to illustrate an example where a sloped wind inflow illustrated by the arrows 98 is in this case measured by a LiDAR with circular scan pattern 100. This should be related to the optimal wind inflow angle 96 to the rotor 10

FIG. 19B serves to illustrate an example where a sloped wind inflow illustrated by the arrows 98 is in this case measured by a 4 beam LiDAR with linear scan pattern 102. This should be related to the optimal wind inflow angle 96 to the rotor 10

FIG. 20A illustrates the collected measurements shown as a large number of dots each representing the average value of a three minutes measurement period regarding wind speed measured in meters/second (y axes) and yaw misalignment angle in degrees (x axes), the vertical dotted line 106 representing the neutral angle misalignment axes—where the average yaw misalignment value shown by the line 108 is about 7°.

Otherwise in FIG. 20B showing measurements after the WTG controller 22 receive and take into consideration signals and data from the condition monitoring box 26—where most of the collected measurement after correction are placed close to the vertical line 108 representing the average yaw misalignment angle of about 0°.

FIG. 21 illustrates collected measurements in a traditional power curve view format from a 3 MW WTG shown as a large number of dots each representing an average from a 3 minutes measurement period regarding wind speed measured in meters/second (x axes) and actual average power produced kW in the corresponding 3 minutes measurement period (y axes). The power curve to the right 110 represents the actual measured power curve before the condition monitoring box 26 is introduced.

The power curve to the left 112 represents the power curve as expected after the condition monitoring box 26 is interconnected to and new information taken into consider-ations by the WTG controller 22 according to the present invention. Collection and processing of data from the new instruments can also be done directly in the WTG controller 22.

Park and fleet analysis: Input and output from the condition monitoring boxes will eventually be stored in a local database and a global database for every single wind turbine in the specific wind farms. Afterwards it will be possible to extract, sort and compare data for an ongoing optimization of the condition monitoring box technical methods and algorithms and for further analysis and statistical materials.

FIGS. 22A and 22B show an schematic overview of overall input and diagnostic of an example embodiment. Time stamped generator torque measurements.

FIG. 22C shows examples on actions associated with the diagnostic of the example embodiment in FIGS. 22A and 22B.

REFERENCE NUMBERS IN THE DRAWING

2 Wind turbine rotor blades
4 Nacelle
6 Spinner/hub
8 Tower
10 Rotor (spinner/hub 6 on which at least one rotor blade 2 is mounted).
12 Wind Turbine Generator (WTG) (its main components are nacelle 4+tower 8+rotor 10+foundation 14)
14 Foundation for the tower 8
16 Main shaft
18 Gearbox
19 High speed shaft connecting gearbox 18 and generator 20
20 Generator
22 WTG Controller (Typically located inside the tower 8 in the bottom)
24 Wind speed and wind direction measurement instrument located on the nacelle 4 behind the rotor 10
26 Condition monitoring box
28 Accelerometers, sensors installed in the hub, on rotor blades, on main shaft and in the nacelle located in the centre of the tower providing position-dependent measurements of movements, accelerations, angles of rotation of the rotor, the individual rotor blades and the tower in x, y and z axes
29 Torque measurement measuring torque on the generator
30 Generator power production measurement
32 LiDAR (Light Detection And Ranging) with at least one laser beam, a spinner anemometer or any other instrument which can measure wind speed and turbulence and potentially also yaw misalignment and wind inflow angle etc. in front of or on the rotor 10
34 Line representing laser beam from LiDAR 32
35 Drive train in a WTG 12. Could be a gearless drive train (hub/spinner 6, main rotor shaft 16 and generator 20) or a traditional drive train (hub/spinner 6, main rotor shaft 16, gear box 18, high speed shaft 19 and generator 20)
36 Nacelle based GPS position tilt and direction compass system or any other instrument or alternative system that reliably can measure the true nacelle/drive train direction
38 Minimum 2 antennas connected to a GPS position, tilt and direction system.
40 Dotted interaction arrow
42 Double interaction arrow
44 Satellite based communication system
46 Minimum 1 antenna connected to satellite based communication system 48 Optional interfaces for additional condition monitoring technologies
50 Short time power supply back up
52 Power supply
54 WAN interface
56 Terminal interface
58 GPRS/3G/4G/5G or any other or any other high-throughput data transfer system interface.
60 USB interface
62 WTG controller 22 interface
64 Line illustrate connection in between condition monitoring box 26 and WTG controller 22
66 Line and cloud illustrates distribution of instant alarm via satellite and data transfer options from/to condition monitoring box 26 via/GPRS/3G/4G/5G/SMS/high-throughput Satellite system/Internet or any other high-throughput data transfer system.
68 Instant alarm transferred and received by owner/operator
70 Instant alarm transferred and received on mobile device
72 Instant alarm and data transferred and received by local server and stored for further analysis and statistics
74 Instant alarm and data transferred from local server to global server using high throughput data transfer system.
76 Instant alarm and data transfer received by global server and stored for further analysis and statistics
78 Arrow representing surrounding wind sectors
80 Dotted circle illustrating the swept area by the rotor 10
82 Fat dotted line illustrating the horizontal direction (with respect to rotor plane)
84 Fat dotted line illustrating the tangential direction (with respect to rotor plane)
86 Wind direction arrow
88 "Blocking effect in front of the rotor 10" Contours of the normalized mean stream wise velocity ($u/u_h$) in the horizontal plane 82 (with respect to rotor plane) at hub 6 height in the vicinity of the zero-yawed turbine (Wake conference 2015—Journal of Physics: Conference Series 625 (2015) 012014 FIG. 5.)
90 "Wake effect behind the rotor 10"—Contours of the normalized mean stream wise velocity ($u/u_h$) in the horizontal plane 82 (with respect to rotor plane) at hub 6 height in the vicinity of the zero-yawed turbine (Wake conference 2015 Journal of Physics: Conference Series 625 (2015) 012014 FIG. 5.)
92 "Blocking effect in front of the rotor 10" Contours of the normalized mean stream wise velocity ($u/u_h$) in the horizontal plane 82 (with respect to rotor plane) at hub 6 height in the vicinity of the turbine operating with 30° yaw misalignment angle (Wake conference 2015—Journal of Physics: Conference Series 625 (2015) 012014 FIG. 12.)
94 "Wake effect behind the rotor 10" Contours of the normalized mean stream wise velocity ($u/u_h$) in the horizontal plane 82 (with respect to rotor plane) at hub 6 height in the vicinity of the turbine operating with 30° yaw misalignment angle (Wake conference 2015—Journal of Physics: Conference Series 625 (2015) 012014 FIG. 12.)
96 Optimal wind inflow angle illustrated by the dotted line
98 Sloped wind inflow angle illustrated by the arrows
100 LiDAR 32 with circular scan pattern
102 LiDAR 32 with 4 beams and linear scan pattern
104 Nacelle 4/drive train 35 direction (dotted line)
106 Dotted line representing 0° yaw misalignment
108 Line representing average yaw misalignment value
110 Power curve before for 3 MW WTG (measured with nacelle based LiDAR 32)
112 Power curve after for 3 MW WTG (measured with nacelle based LiDAR 32)
114 Top position for the blade 2 in the swept area 80 of the rotor 10
116 Bottom position for the blade 2 in the swept area 80 of the rotor 10
118 Contours of the expected "Blocking effect zone" in front of the rotor 10 normalized mean stream wise velocity ($u/u_h$) in the tangential plane 84 (with respect to rotor plane) in the vicinity of the turbine operating with 0° yaw misalignment angle.
120 Line representing the 7° tilt angle (horizontally) of mounting for the nacelle 4/the drive train 35/the rotor 10 with respect to the tower 8.
122 Length of the lines showing the expected wind speed relatively in the tangential plane 84 under normal circumstances will be increasing when the height above the terrain increases.

What is claimed is:

1. A method of condition monitoring a wind turbine generator comprising acts of:
   collecting at least the following data sets with time stamps:
   A) generator power production measurements;
   B) mechanical status measurements;
   C) nacelle direction measurements;
   D) meteorological conditions measurement including at least wind condition measurements;
   E) and torque measurement
   synchronizing and Processing the data sets to provide at least
   i) Rotor/blade status information
   ii) Generator power production information
   iii) Tower status information
   classifying the information i), ii) and iii) in at least the following states of operation:
   Normal state of operation or
   Non-normal state of operation, characterized in, that the said act of synchronization is performed in at least one synchronization system for synchronizing collected and time stamped data; and
   controlling the wind turbine generator by feeding the processed at least one:
   i) Rotor/blade status information
   ii) Generator power production information
   iii) Tower status information to a wind turbine generator controller conditionally based on the at least the classified states of operation.

2. The method of condition monitoring according to claim 1, wherein the data sets A), B), C) and D) are collected, time stamped, stored and synchronized.

3. The method of conditioning monitoring according to claim 1 wherein the act of classifying includes at least one automatic self-calibrating processing of parameters for the classification of the state of operation being adjusted to the individual wind turbine.

4. The method of condition monitoring according to claim 1, wherein yaw misalignment is classified as a normal state of operation.

5. The method of condition monitoring according to claim 1, wherein an act of processing data to provide Yaw misalignment and/or Tower status information is via acts of:
   Processing data to provide
   i) Rotor/blade status information,
   ii) generator power production information from
   A) power production measurements
   B) mechanical status measurements or load.

6. The method of condition monitoring according to claim 5, wherein the act of processing data to provide yaw misalignment information and/or tower status information and/or information about wind gusts approaching the wind turbine is via acts of:
- collecting C) nacelle direction measurements and/or D) meteorological conditions measurements from
  - a permanently or temporally installed high precision system
  - a permanently installed lower precision system corrected/calibrated to the high precision system.

7. The method of condition monitoring according to claim 1, wherein the acts of
- Collecting involves acts of collecting
  - A) time stamped generator power production measurements that are synchronized with
  - B) time stamped sensory input including
    - Hub sensory input
    - Rotor blade sensory input
    - Main Shaft sensory input
    - Nacelle sensory input
- and where the act of
  - processing involves assessing one or more of:
    - Rotor imbalance
    - Individual blade imbalance
    - Yaw alignment
    - Icing on blades
    - Contamination of blade
    - Individual blade damage
    - Pitch bearing damage
    - Electrical or hydraulic Pitch error
    - Unbalanced mass of individual blades
    - Improved (increased or reduced) generator power production from yawing
    - Improved (increased or reduced) generator power production from pitching blades
    - Actual Yawed wind inflow angle
    - Actual turbulence
    - Actual Sloped wind inflow angle
    - Actual horizontal wind shear
    - Abnormal movements in tower
    - Generator power production classification
    - Wind gust approaching the rotor.

8. A method of operating a wind turbine generator with the wind turbine generator controller based on conditioning monitoring according to claim 1, wherein the method of operation involves acts of:
- Controlling the wind turbine generator by feeding the processed at least:
  - i) Rotor/blade status information
  - ii) Generator power production information
  - iii) Tower status information
- to the wind turbine generator controller conditionally based on at least the classified states of operation:
  - Normal state of operation
  - Non-normal state of operation.

9. The method of operating a wind turbine generator according to claim 8, wherein the states of operation of:
- Normal state of operation
  - allows operation where no corrective action signals are applied to the wind turbine generator controller or where corrective action signals are applied to the wind turbine generator controller;
- Non-normal state of operation
  - raises a flag/an alarm requiring the act of manual attendance for continued operation of the wind turbine generator.

10. The method of operating a wind turbine generator according to claim 8, wherein the state of operation of:
- Normal state of operation
  - involves operating the WTG with yaw misalignment.

11. The method of operating a wind turbine generator according to claim 8, wherein the state of operation of:
- Non-normal state of operation requires the act of automatic stop of continued operation of the wind turbine generator and an act of inspecting the wind turbine generator before normal state of operation is resumed.

12. The method of operating a wind turbine generator according to claim 8, wherein the state of operation of:
- Non-normal state of operation requires visually inspecting the wind turbine generator by acts of:
  - pointing a visual inspection system with a field of view about a line of sight of a plane where the rotor blade, the rotor system and the tower during still stand, start up and during operation will be present;
  - capturing multiple images of the field of view with at least multiple images with at least part of the rotor blade, the rotor system and the tower in the image;
  - selecting at least one reference image amongst the captured images;
  - comparing at least one other captured image with the reference image.

13. The method of operating a wind turbine generator according to claim 8, wherein the method of operation involves acts of controlling the wind turbine generator by feeding the processed at least information for improved (increased or reduced) generator power production from yawing to the wind turbine generator controller for automatically controlling alignment (yawing) of the wind turbine generator nacelle to position the rotor in the optimal wind direction based on improvement of generator power production during yawing such that a wind turbine generator yaw controller in sequence forces yawing in different directions to search for optimum of generator power production and there by optimal yaw alignment.

14. The method of operating a wind turbine generator according to claim 8, wherein the method of operation involves acts of controlling the wind turbine generator by feeding the processed information for improved (increased or reduced) generator power production from pitching blades to the wind turbine generator controller for controlling wind turbine generator blade pitch automatically to positioning the blade in an optimal angle based on improvement of generator power production during blade pitching.

15. The method of operating a wind turbine generator according to claim 8, wherein the method of operation involves acts of controlling the wind turbine generator by feeding the processed information about gusts approaching the wind turbine by controlling WTG blade to pitch automatically to positioning the blade in an optimal angle based on improved load control reducing loads from peak wind gusts.

16. The method of condition monitoring according to claim 1, comprising a further act of visually inspecting a wind turbine generator comprising the acts of:
- pointing a visual inspection system with a field of view about a line of sight of a plane where the rotor blade, the rotor system and the tower during still stand, start up and during operation will be present;
- capturing multiple images of the field of view with at least multiple images with at least part of the rotor blade, the rotor system and the tower in the image;
- selecting at least one reference image amongst the captured images;

comparing at least one other captured image with the reference image.

17. The method of condition monitoring according to claim 16, where the visual inspection is carried out by means of one or more line scan cameras.

18. The method of condition monitoring according to claim 16, where the visual inspection is carried out by means of one or more line scan cameras and one or more area scan cameras.

19. The method of condition monitoring according to claim 18 where one or more line scan camera is used as a trigger unit to activate one or more area scan camera.

20. The method of condition monitoring according to claim 17, where phase lock loop technology is used for triggering and activation of either one or more line scan cameras and/or one or more area scan camera based on software or methods to synchronize a computer to the real rotor.

21. A wind turbine generator condition monitoring system comprising:
   data set collection means for collecting data sets with time stamps from
      A) means for measuring generator power production output;
      B) means for measuring mechanical status;
      C) means for measuring nacelle direction;
      D) means for measuring meteorological conditions including at least wind condition measurements;
      E) means for measuring torque conditions for the generator;
   means for synchronizing and Processing the data sets to provide at least
      i) Rotor/blade status information
      ii) Generator power production information
      iii) Tower status information
   means for classifying the information i), ii) and iii) in at least the following states of operation:
      Normal state of operation or
      Non-normal state of operation,
   characterized in, that the said means of synchronization is performed in at least one synchronization system for synchronizing the collected and time stamped data; and
   at least one processor configured to process the collected data sets and functionally to generate an output for controlling the wind turbine generator by feeding of one or more of the:
      i) Rotor/blade status information
      ii) Generator power production information
      iii) Tower status information
      to a wind turbine controller generator conditionally based on the at least the classified states of operation.

22. A wind turbine generator condition monitoring system according to claim 21, further comprising
   at least one synchronization system for synchronizing collected and time stamped data and
   optionally to provide information for improved (increased or reduced) generator power production from yawing to be used for automatic control of yawing and other purposes;
   optionally to provide information for improved (increased or reduced) generator power production from pitching blades to be used for automatic control of blade pitching and other purposes; and
   optional optionally provide information for improved load reduction control by pitching blades to avoid loads from high gusts approaching the wind turbine.

23. A wind turbine generator condition monitoring system according to claim 21, further comprising at least one automatic self-calibrating processing of parameters for the classification of the state of operation being adjusted to the individual wind turbine.

* * * * *